United States Patent
Pestano et al.

(10) Patent No.: US 10,407,736 B2
(45) Date of Patent: Sep. 10, 2019

(54) EXPRESSION OF ETS RELATED GENE (ERG) AND PHOSPHATASE AND TENSIN HOMOLOG (PTEN) CORRELATES WITH PROSTATE CANCER CAPSULAR PENETRATION

(71) Applicants: Ventana Medical Systems, Inc., Tucson, AZ (US); The Arizona Board of Regents on behalf of the University of Arizona, Tucson, AZ (US)

(72) Inventors: Gary Pestano, Lafayette, CO (US); Ray B. Nagle, Tucson, AZ (US); Connie Cortez, Tucson, AZ (US); Kristie A. Vanpatten, Oro Valley, AZ (US); Amit M. Algotar, Tucson, AZ (US)

(73) Assignees: Ventana Medical Systems, Inc., Tucson, AZ (US); The Arizona Board of Regents on behalf of the University of Arizona, Tucson, AZ (US)

( * ) Notice: Subject to any disclaimer, the term of this patent is extended or adjusted under 35 U.S.C. 154(b) by 126 days.

(21) Appl. No.: 15/242,011

(22) Filed: Aug. 19, 2016

(65) Prior Publication Data
US 2016/0355891 A1    Dec. 8, 2016

Related U.S. Application Data

(62) Division of application No. 13/596,266, filed on Aug. 28, 2012, now Pat. No. 9,435,812.

(60) Provisional application No. 61/529,691, filed on Aug. 31, 2011.

(51) Int. Cl.
*C12Q 1/6886* (2018.01)
*G01N 33/68* (2006.01)
*G01N 33/574* (2006.01)

(52) U.S. Cl.
CPC ....... *C12Q 1/6886* (2013.01); *G01N 33/5748* (2013.01); *G01N 33/57434* (2013.01); *G01N 33/6893* (2013.01); *C12Q 2600/118* (2013.01); *C12Q 2600/158* (2013.01); *C12Q 2600/16* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 9,435,812 B2 | 9/2016 | Pestano et al. | |
| 2002/0052001 A1* | 5/2002 | Cousens | C07K 14/705 435/7.1 |
| 2002/0197656 A1* | 12/2002 | Li | B01J 19/0046 435/7.21 |
| 2008/0293070 A1* | 11/2008 | Sekaly | G01N 33/505 435/6.16 |
| 2010/0285001 A1* | 11/2010 | Land | C12Q 1/6886 424/130.1 |
| 2013/0071843 A1* | 3/2013 | Squire | C12Q 1/6841 435/6.11 |
| 2013/0196866 A1 | 8/2013 | Pestano et al. | |

FOREIGN PATENT DOCUMENTS

WO    WO 2005/113816 A2    12/2005

OTHER PUBLICATIONS

"GeneChip Human Genome U133 Set," Internet Citation, XP002232760, retrieved from the Internet: URL:http://www.affymetrix.com/support/technical/datasheets/hgu133_datasheet.pdf, retrieved Feb. 26, 2003 (Abstract).
"Human Genome U95Av2," Internet Citation, XP002215481, retrieved from the Internet: URL:http://www.affymetrix.com, retrieved Oct. 2, 2002 (Abstract).
Brosh et al., "Correlation Between ERB Rearrangement and Pten Loss with Capsular Penetration in Prostate Cancer," *Eur. Urology Suppl.* 11:E427-E427a, 2012.
Carver et al., "Aberrant ERG Expression Cooperates with Loss of PTEN to Promote Cancer Progression in the Prostate," *Nature Genet.* 41:619-624, 2009.
Carver et al., "Aberrant ERG Expression Cooperates with Pten Loss to Promote Prostate Tumorigenesis," *J. Urol.* 179:460, 2008 (abstract 1342).
Constantine and Harrington, "Use of GeneChip High-Density Oligonucleotide Arrays for Gene Expression Monitoring," *Life Science News*, Amersham Life Science, US, pp. 11-14, 1998.
Dittamore et al., "PL-01 Plenary Oral Free Paper Session: Investigation of the Correlation Between Up-Regulated ERG Expression and PTEN Loss with Capsular Penetration in Prostate Cancer," *Virchows Arch.* 459:S1-S329, 2011.
Ernst et al., "Decrease and Gain of Gene Expression Are Equally Discriminatory Markers for Prostate Carcinoma," *Am. J. Pathol.* 160:2169-2180, 2002.
Petrovics et al., "Frequent Overexpression of ETS-Related Gene-1 (ERG1) in Prostate Cancer Transcriptome," *Oncogene* 24:3847-3852, 2005.
Reid et al., "Molecular Characterisation of ERG, ETVI and PTEN Gene Loci Identifies Patients at Low and High Risk of Death from Prostate Cancer," *Br. J. Cancer* 102:678-684, 2010.

(Continued)

Primary Examiner — Changhwa J Cheu
(74) Attorney, Agent, or Firm — Klarquist Sparkman, LLP

(57) ABSTRACT

The disclosure provides methods for characterizing a prostate cancer sample by detecting expression of ERG, PTEN or both, changes in which relative to a normal control are shown herein to be correlated with prostate cancer capsular penetration and more aggressive forms of prostate cancer. Such methods are useful for the prognosis of prostate cancer capsular penetration and for making treatment decisions in patients with prostate cancer that has penetrated the capsule. Also provided are kits that can be used with such methods.

18 Claims, 5 Drawing Sheets
Specification includes a Sequence Listing.

(56) References Cited

OTHER PUBLICATIONS

Trotman et al., "PTEN Dose Dictates Cancer Progression in the Prostate," *PLoS Biol.* 1:385-396, 2003.
Yoshimoto et al., "Absence of TMPRSS2:ERG Fusions and PTEN Losses in Prostate Cancer is Associated with a Favorable Outcome," *Mod. Pathol.* 21:1451-1460, 2008.
PCTUS2012052627 International Search Report dated Dec. 17, 2012 (7 pages).
PCTUS2012052627 Written Opinion dated Dec. 17, 2012 (9 pages).

* cited by examiner

SEQUENCE LISTING

<160> NUMBER OF SEQ ID NOS: 11

<210> SEQ ID NO 1
<211> LENGTH: 1461
<212> TYPE: DNA
<213> ORGANISM: Homo sapiens
<220> FEATURE:
<221> NAME/KEY: CDS
<222> LOCATION: (1)..(1461)

<400> SEQUENCE: 1

```
atg att cag act gtc ccg gac cca gca gct cat atc aag gaa gcc tta      48
Met Ile Gln Thr Val Pro Asp Pro Ala Ala His Ile Lys Glu Ala Leu
1               5                  10                  15 tca gtt gtg agt gag gac cag tcg ttg ttt gag tgt gcc tac gga acg      96
Ser Val Val Ser Glu Asp Gln Ser Leu Phe Glu Cys Ala Tyr Gly Thr
                20                  25                  30 cca cac ctg gct aag aca gag atg acc gcg tcc tcc tcc agc gac tat     144
Pro His Leu Ala Lys Thr Glu Met Thr Ala Ser Ser Ser Ser Asp Tyr
            35                  40                  45 gga cag act tcc aag atg agc cca cgc gtc cct cag cag gat tgg ctg     192
Gly Gln Thr Ser Lys Met Ser Pro Arg Val Pro Gln Gln Asp Trp Leu
        50                  55                  60 tct caa ccc cca gcc agg gtc acc atc aaa atg gaa tgt aac cct agc     240
Ser Gln Pro Pro Ala Arg Val Thr Ile Lys Met Glu Cys Asn Pro Ser
65                  70                  75                  80 cag gtg aat ggc tca agg aac tct cct gat gaa tgc agt gtg gcc aaa     288
Gln Val Asn Gly Ser Arg Asn Ser Pro Asp Glu Cys Ser Val Ala Lys
                85                  90                  95 ggc ggg aag atg gtg ggc agc cca gac acc gtt ggg atg aac tac ggc     336
Gly Gly Lys Met Val Gly Ser Pro Asp Thr Val Gly Met Asn Tyr Gly
                100                 105                 110 agc tac atg gag gag aag cac atg cca ccc cca aac atg acc acg aac     384
Ser Tyr Met Glu Glu Lys His Met Pro Pro Pro Asn Met Thr Thr Asn
            115                 120                 125 gag cgc aga gtt atc gtg cca gca gat cct acg cta tgg agt aca gac     432
Glu Arg Arg Val Ile Val Pro Ala Asp Pro Thr Leu Trp Ser Thr Asp
        130                 135                 140 cat gtg cgg cag tgg ctg gag tgg gcg gtg aaa gaa tat ggc ctt cca     480
His Val Arg Gln Trp Leu Glu Trp Ala Val Lys Glu Tyr Gly Leu Pro
145                 150                 155                 160 gac gtc aac atc ttg tta ttc cag aac atc gat ggg aag gaa ctg tgc     528
Asp Val Asn Ile Leu Leu Phe Gln Asn Ile Asp Gly Lys Glu Leu Cys
                165                 170                 175 aag atg acc aag gac gac ttc cag agg ctc acc ccc agc tac aac gcc     576
Lys Met Thr Lys Asp Asp Phe Gln Arg Leu Thr Pro Ser Tyr Asn Ala
                180                 185                 190 gac atc ctt ctc tca cat ctc cac tac ctc aga gag act cct ctt cca     624
Asp Ile Leu Leu Ser His Leu His Tyr Leu Arg Glu Thr Pro Leu Pro
            195                 200                 205 cat ttg act tca gat gat gtt gat aaa gcc tta caa aac tct cca cgg     672
His Leu Thr Ser Asp Asp Val Asp Lys Ala Leu Gln Asn Ser Pro Arg
        210                 215                 220 tta atg cat gct aga aac aca ggg ggt gca gct ttt att ttc cca aat     720
Leu Met His Ala Arg Asn Thr Gly Gly Ala Ala Phe Ile Phe Pro Asn
225                 230                 235                 240 act tca gta tat cct gaa gct acg caa aga att aca act agg cca gat     768
Thr Ser Val Tyr Pro Glu Ala Thr Gln Arg Ile Thr Thr Arg Pro Asp
                245                 250                 255 tta cca tat gag ccc ccc agg aga tca gcc tgg acc ggt cac ggc cac     816
Leu Pro Tyr Glu Pro Pro Arg Arg Ser Ala Trp Thr Gly His Gly His
```

| | | | | | | | | | | | | | | | | |
|---|---|---|---|---|---|---|---|---|---|---|---|---|---|---|---|---|
| | | | 260 | | | | | 265 | | | | | 270 | | | |
| ccc | acg | ccc | cag | tcg | aaa | gct | gct | caa | cca | tct | cct | tcc | aca | gtg | ccc | 864 |
| Pro | Thr | Pro | Gln | Ser | Lys | Ala | Ala | Gln | Pro | Ser | Pro | Ser | Thr | Val | Pro | |
| | | 275 | | | | | 280 | | | | | 285 | | | | |
| aaa | act | gaa | gac | cag | cgt | cct | cag | tta | gat | cct | tat | cag | att | ctt | gga | 912 |
| Lys | Thr | Glu | Asp | Gln | Arg | Pro | Gln | Leu | Asp | Pro | Tyr | Gln | Ile | Leu | Gly | |
| | 290 | | | | | 295 | | | | | 300 | | | | | |
| cca | aca | agt | agc | cgc | ctt | gca | aat | cca | ggc | agt | ggc | cag | atc | cag | ctt | 960 |
| Pro | Thr | Ser | Ser | Arg | Leu | Ala | Asn | Pro | Gly | Ser | Gly | Gln | Ile | Gln | Leu | |
| 305 | | | | | 310 | | | | | 315 | | | | | 320 | |
| tgg | cag | ttc | ctc | ctg | gag | ctc | ctg | tcg | gac | agc | tcc | aac | tcc | agc | tgc | 1008 |
| Trp | Gln | Phe | Leu | Leu | Glu | Leu | Leu | Ser | Asp | Ser | Ser | Asn | Ser | Ser | Cys | |
| | | | 325 | | | | | 330 | | | | | 335 | | | |
| atc | acc | tgg | gaa | ggc | acc | aac | ggg | gag | ttc | aag | atg | acg | gat | ccc | gac | 1056 |
| Ile | Thr | Trp | Glu | Gly | Thr | Asn | Gly | Glu | Phe | Lys | Met | Thr | Asp | Pro | Asp | |
| | | 340 | | | | | 345 | | | | | 350 | | | | |
| gag | gtg | gcc | cgg | cgc | tgg | gga | gag | cgg | aag | agc | aaa | ccc | aac | atg | aac | 1104 |
| Glu | Val | Ala | Arg | Arg | Trp | Gly | Glu | Arg | Lys | Ser | Lys | Pro | Asn | Met | Asn | |
| | 355 | | | | | 360 | | | | | 365 | | | | | |
| tac | gat | aag | ctc | agc | cgc | gcc | ctc | cgt | tac | tac | tat | gac | aag | aac | atc | 1152 |
| Tyr | Asp | Lys | Leu | Ser | Arg | Ala | Leu | Arg | Tyr | Tyr | Tyr | Asp | Lys | Asn | Ile | |
| | 370 | | | | | 375 | | | | | 380 | | | | | |
| atg | acc | aag | gtc | cat | ggg | aag | cgc | tac | gcc | tac | aag | ttc | gac | ttc | cac | 1200 |
| Met | Thr | Lys | Val | His | Gly | Lys | Arg | Tyr | Ala | Tyr | Lys | Phe | Asp | Phe | His | |
| 385 | | | | | 390 | | | | | 395 | | | | | 400 | |
| ggg | atc | gcc | cag | gcc | ctc | cag | ccc | cac | ccc | ccg | gag | tca | tct | ctg | tac | 1248 |
| Gly | Ile | Ala | Gln | Ala | Leu | Gln | Pro | His | Pro | Pro | Glu | Ser | Ser | Leu | Tyr | |
| | | | | 405 | | | | | 410 | | | | | 415 | | |
| aag | tac | ccc | tca | gac | ctc | ccg | tac | atg | ggc | tcc | tat | cac | gcc | cac | cca | 1296 |
| Lys | Tyr | Pro | Ser | Asp | Leu | Pro | Tyr | Met | Gly | Ser | Tyr | His | Ala | His | Pro | |
| | | | 420 | | | | | 425 | | | | | 430 | | | |
| cag | aag | atg | aac | ttt | gtg | gcg | ccc | cac | cct | cca | gcc | ctc | ccc | gtg | aca | 1344 |
| Gln | Lys | Met | Asn | Phe | Val | Ala | Pro | His | Pro | Pro | Ala | Leu | Pro | Val | Thr | |
| | | 435 | | | | | 440 | | | | | 445 | | | | |
| tct | tcc | agt | ttt | ttt | gct | gcc | cca | aac | cca | tac | tgg | aat | tca | cca | act | 1392 |
| Ser | Ser | Ser | Phe | Phe | Ala | Ala | Pro | Asn | Pro | Tyr | Trp | Asn | Ser | Pro | Thr | |
| | 450 | | | | | 455 | | | | | 460 | | | | | |
| ggg | ggt | ata | tac | ccc | aac | act | agg | ctc | ccc | acc | agc | cat | atg | cct | tct | 1440 |
| Gly | Gly | Ile | Tyr | Pro | Asn | Thr | Arg | Leu | Pro | Thr | Ser | His | Met | Pro | Ser | |
| 465 | | | | | 470 | | | | | 475 | | | | | 480 | |
| cat | ctg | ggc | act | tac | tac | taa | | | | | | | | | | 1461 |
| His | Leu | Gly | Thr | Tyr | Tyr | | | | | | | | | | | |
| | | | | 485 | | | | | | | | | | | | |

<210> SEQ ID NO 2
<211> LENGTH: 486
<212> TYPE: PRT
<213> ORGANISM: Homo sapiens

<400> SEQUENCE: 2

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser

-continued

```
                65                  70                  75                  80
        Gln Val Asn Gly Ser Arg Asn Ser Pro Asp Glu Cys Ser Val Ala Lys
                            85                  90                  95
        Gly Gly Lys Met Val Gly Ser Pro Asp Thr Val Gly Met Asn Tyr Gly
                            100                 105                 110
        Ser Tyr Met Glu Glu Lys His Met Pro Pro Asn Met Thr Thr Asn
                            115                 120                 125
        Glu Arg Arg Val Ile Val Pro Ala Asp Pro Thr Leu Trp Ser Thr Asp
                            130                 135                 140
        His Val Arg Gln Trp Leu Glu Trp Ala Val Lys Glu Tyr Gly Leu Pro
        145                 150                 155                 160
        Asp Val Asn Ile Leu Leu Phe Gln Asn Ile Asp Gly Lys Glu Leu Cys
                            165                 170                 175
        Lys Met Thr Lys Asp Asp Phe Gln Arg Leu Thr Pro Ser Tyr Asn Ala
                            180                 185                 190
        Asp Ile Leu Leu Ser His Leu His Tyr Leu Arg Glu Thr Pro Leu Pro
                            195                 200                 205
        His Leu Thr Ser Asp Asp Val Asp Lys Ala Leu Gln Asn Ser Pro Arg
            210                 215                 220
        Leu Met His Ala Arg Asn Thr Gly Gly Ala Ala Phe Ile Phe Pro Asn
        225                 230                 235                 240
        Thr Ser Val Tyr Pro Glu Ala Thr Gln Arg Ile Thr Thr Arg Pro Asp
                            245                 250                 255
        Leu Pro Tyr Glu Pro Pro Arg Arg Ser Ala Trp Thr Gly His Gly His
                            260                 265                 270
        Pro Thr Pro Gln Ser Lys Ala Ala Gln Pro Ser Pro Ser Thr Val Pro
            275                 280                 285
        Lys Thr Glu Asp Gln Arg Pro Gln Leu Asp Pro Tyr Gln Ile Leu Gly
                            290                 295                 300
        Pro Thr Ser Ser Arg Leu Ala Asn Pro Gly Ser Gly Gln Ile Gln Leu
        305                 310                 315                 320
        Trp Gln Phe Leu Leu Glu Leu Leu Ser Asp Ser Ser Asn Ser Ser Cys
                            325                 330                 335
        Ile Thr Trp Glu Gly Thr Asn Gly Glu Phe Lys Met Thr Asp Pro Asp
                            340                 345                 350
        Glu Val Ala Arg Arg Trp Gly Glu Arg Lys Ser Lys Pro Asn Met Asn
                            355                 360                 365
        Tyr Asp Lys Leu Ser Arg Ala Leu Arg Tyr Tyr Asp Lys Asn Ile
            370                 375                 380
        Met Thr Lys Val His Gly Lys Arg Tyr Ala Tyr Lys Phe Asp Phe His
        385                 390                 395                 400
        Gly Ile Ala Gln Ala Leu Gln Pro His Pro Glu Ser Ser Leu Tyr
                            405                 410                 415
        Lys Tyr Pro Ser Asp Leu Pro Tyr Met Gly Ser Tyr His Ala His Pro
                            420                 425                 430
        Gln Lys Met Asn Phe Val Ala Pro His Pro Ala Leu Pro Val Thr
                            435                 440                 445
        Ser Ser Ser Phe Phe Ala Ala Pro Asn Pro Tyr Trp Asn Ser Pro Thr
            450                 455                 460
        Gly Gly Ile Tyr Pro Asn Thr Arg Leu Pro Thr Ser His Met Pro Ser
        465                 470                 475                 480
        His Leu Gly Thr Tyr Tyr
                            485
```

```
<210> SEQ ID NO 3
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 3
```

| | | | | | | | | | | | | | | | | |
|---|---|---|---|---|---|---|---|---|---|---|---|---|---|---|---|---|
| atg | aca | gcc | atc | atc | aaa | gag | atc | gtt | agc | aga | aac | aaa | agg | aga | tat | 48 |
| Met | Thr | Ala | Ile | Ile | Lys | Glu | Ile | Val | Ser | Arg | Asn | Lys | Arg | Arg | Tyr | |
| 1 | | | | 5 | | | | | 10 | | | | | 15 | | |
| caa | gag | gat | gga | ttc | gac | tta | gac | ttg | acc | tat | att | tat | cca | aac | att | 96 |
| Gln | Glu | Asp | Gly | Phe | Asp | Leu | Asp | Leu | Thr | Tyr | Ile | Tyr | Pro | Asn | Ile | |
| | | | 20 | | | | | 25 | | | | | 30 | | | |
| att | gct | atg | gga | ttt | cct | gca | gaa | aga | ctt | gaa | ggc | gta | tac | agg | aac | 144 |
| Ile | Ala | Met | Gly | Phe | Pro | Ala | Glu | Arg | Leu | Glu | Gly | Val | Tyr | Arg | Asn | |
| | | | 35 | | | | 40 | | | | | 45 | | | | |
| aat | att | gat | gat | gta | gta | agg | ttt | ttg | gat | tca | aag | cat | aaa | aac | cat | 192 |
| Asn | Ile | Asp | Asp | Val | Val | Arg | Phe | Leu | Asp | Ser | Lys | His | Lys | Asn | His | |
| | 50 | | | | | 55 | | | | | 60 | | | | | |
| tac | aag | ata | tac | aat | ctt | tgt | gct | gaa | aga | cat | tat | gac | acc | gcc | aaa | 240 |
| Tyr | Lys | Ile | Tyr | Asn | Leu | Cys | Ala | Glu | Arg | His | Tyr | Asp | Thr | Ala | Lys | |
| 65 | | | | | 70 | | | | | 75 | | | | | 80 | |
| ttt | aat | tgc | aga | gtt | gca | caa | tat | cct | ttt | gaa | gac | cat | aac | cca | cca | 288 |
| Phe | Asn | Cys | Arg | Val | Ala | Gln | Tyr | Pro | Phe | Glu | Asp | His | Asn | Pro | Pro | |
| | | | | 85 | | | | | 90 | | | | | 95 | | |
| cag | cta | gaa | ctt | atc | aaa | ccc | ttt | tgt | gaa | gat | ctt | gac | caa | tgg | cta | 336 |
| Gln | Leu | Glu | Leu | Ile | Lys | Pro | Phe | Cys | Glu | Asp | Leu | Asp | Gln | Trp | Leu | |
| | | | 100 | | | | | 105 | | | | | 110 | | | |
| agt | gaa | gat | gac | aat | cat | gtt | gca | gca | att | cac | tgt | aaa | gct | gga | aag | 384 |
| Ser | Glu | Asp | Asp | Asn | His | Val | Ala | Ala | Ile | His | Cys | Lys | Ala | Gly | Lys | |
| | | | 115 | | | | 120 | | | | | 125 | | | | |
| gga | cga | act | ggt | gta | atg | ata | tgt | gca | tat | tta | tta | cat | cgg | ggc | aaa | 432 |
| Gly | Arg | Thr | Gly | Val | Met | Ile | Cys | Ala | Tyr | Leu | Leu | His | Arg | Gly | Lys | |
| | 130 | | | | | 135 | | | | | 140 | | | | | |
| ttt | tta | aag | gca | caa | gag | gcc | cta | gat | ttc | tat | ggg | gaa | gta | agg | acc | 480 |
| Phe | Leu | Lys | Ala | Gln | Glu | Ala | Leu | Asp | Phe | Tyr | Gly | Glu | Val | Arg | Thr | |
| 145 | | | | | 150 | | | | | 155 | | | | | 160 | |
| aga | gac | aaa | aag | gga | gta | act | att | ccc | agt | cag | agg | cgc | tat | gtg | tat | 528 |
| Arg | Asp | Lys | Lys | Gly | Val | Thr | Ile | Pro | Ser | Gln | Arg | Arg | Tyr | Val | Tyr | |
| | | | | 165 | | | | | 170 | | | | | 175 | | |
| tat | tat | agc | tac | ctg | tta | aag | aat | cat | ctg | gat | tat | aga | cca | gtg | gca | 576 |
| Tyr | Tyr | Ser | Tyr | Leu | Leu | Lys | Asn | His | Leu | Asp | Tyr | Arg | Pro | Val | Ala | |
| | | | 180 | | | | | 185 | | | | | 190 | | | |
| ctg | ttg | ttt | cac | aag | atg | atg | ttt | gaa | act | att | cca | atg | ttc | agt | ggc | 624 |
| Leu | Leu | Phe | His | Lys | Met | Met | Phe | Glu | Thr | Ile | Pro | Met | Phe | Ser | Gly | |
| | | | 195 | | | | | 200 | | | | | 205 | | | |
| gga | act | tgc | aat | cct | cag | ttt | gtg | gtc | tgc | cag | cta | aag | gtg | aag | ata | 672 |
| Gly | Thr | Cys | Asn | Pro | Gln | Phe | Val | Val | Cys | Gln | Leu | Lys | Val | Lys | Ile | |
| | 210 | | | | | 215 | | | | | 220 | | | | | |
| tat | tcc | tcc | aat | tca | gga | ccc | aca | cga | cgg | gaa | gac | aag | ttc | atg | tac | 720 |
| Tyr | Ser | Ser | Asn | Ser | Gly | Pro | Thr | Arg | Arg | Glu | Asp | Lys | Phe | Met | Tyr | |
| 225 | | | | | 230 | | | | | 235 | | | | | 240 | |
| ttt | gag | ttc | cct | cag | ccg | tta | cct | gtg | tgt | ggt | gat | atc | aaa | gta | gag | 768 |
| Phe | Glu | Phe | Pro | Gln | Pro | Leu | Pro | Val | Cys | Gly | Asp | Ile | Lys | Val | Glu | |
| | | | | 245 | | | | | 250 | | | | | 255 | | |
| ttc | ttc | cac | aaa | cag | aac | aag | atg | cta | aaa | aag | gac | aaa | atg | ttt | cac | 816 |
| Phe | Phe | His | Lys | Gln | Asn | Lys | Met | Leu | Lys | Lys | Asp | Lys | Met | Phe | His | |
| | | | 260 | | | | | 265 | | | | | 270 | | | |

```
ttt tgg gta aat aca ttc ttc ata cca gga cca gag gaa acc tca gaa    864
Phe Trp Val Asn Thr Phe Phe Ile Pro Gly Pro Glu Glu Thr Ser Glu
        275                 280                 285 aaa gta gaa aat gga agt cta tgt gat caa gaa atc gat agc att tgc    912
Lys Val Glu Asn Gly Ser Leu Cys Asp Gln Glu Ile Asp Ser Ile Cys
        290                 295                 300 agt ata gag cgt gca gat aat gac aag gaa tat cta gta ctt act tta    960
Ser Ile Glu Arg Ala Asp Asn Asp Lys Glu Tyr Leu Val Leu Thr Leu
305                 310                 315                 320 aca aaa aat gat ctt gac aaa gca aat aaa gac aaa gcc aac cga tac   1008
Thr Lys Asn Asp Leu Asp Lys Ala Asn Lys Asp Lys Ala Asn Arg Tyr
                325                 330                 335 ttt tct cca aat ttt aag gtg aag ctg tac ttc aca aaa aca gta gag   1056
Phe Ser Pro Asn Phe Lys Val Lys Leu Tyr Phe Thr Lys Thr Val Glu
                340                 345                 350 gag ccg tca aat cca gag gct agc agt tca act tct gta aca cca gat   1104
Glu Pro Ser Asn Pro Glu Ala Ser Ser Ser Thr Ser Val Thr Pro Asp
                355                 360                 365 gtt agt gac aat gaa cct gat cat tat aga tat tct gac acc act gac   1152
Val Ser Asp Asn Glu Pro Asp His Tyr Arg Tyr Ser Asp Thr Thr Asp
370                 375                 380 tct gat cca gag aat gaa cct ttt gat gaa gat cag cat aca caa att   1200
Ser Asp Pro Glu Asn Glu Pro Phe Asp Glu Asp Gln His Thr Gln Ile
385                 390                 395                 400 aca aaa gtc tga                                                   1212
Thr Lys Val <210> SEQ ID NO 4
<211> LENGTH: 403
<212> TYPE: PRT
<213> ORGANISM: Homo sapiens

<400> SEQUENCE: 4

Met Thr Ala Ile Ile Lys Glu Ile Val Ser Arg Asn Lys Arg Tyr
1               5                   10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190
```

```
Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
tccttcccca tcggtttgtg gc                                              22

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
acgcagagat cagtgaaggg at                                              22

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
```

```
gtttctacac acgttgccca ct                                               22

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
tcaaaaggaa tcacatttac cacgga                                           26

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
tgacaccatg caatcttaaa agctga                                           26

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
tgggaaagga ttgacaacta agagga                                           26

<210> SEQ ID NO 11
<211> LENGTH: 339
<212> TYPE: DNA
<213> ORGANISM: Artificial Sequence
<220> FEATURE:
<223> OTHER INFORMATION: CEN10 specific probe

<400> SEQUENCE: 11
gaattcttct gtctagcagt aaatgagaaa tcccgcttcc aacgaaggcc tcaaacgggt      60
ctaactaatc acttgcagac tttacagaca gagtctttcc aaaactgctct atgaagagaa   120 aggtgaaact ctgtgaactg aacgcacaga tgacaaagca gtttctgaga atgcttctgt    180
gtagttttta cacgaagata tttccatttc aaagattagc ctcaaatcgc ttgaaatctc    240
cacttgcaaa ctccacagaa agaattttc aaaactgctc tgtctaaagg aaggttcaac     300
tctgtgactt gaatacacac aacacaaaga agtgactga                           339
```

EXPRESSION OF ETS RELATED GENE (ERG) AND PHOSPHATASE AND TENSIN HOMOLOG (PTEN) CORRELATES WITH PROSTATE CANCER CAPSULAR PENETRATION

CROSS REFERENCE TO RELATED APPLICATION

This application is a divisional of U.S. application Ser. No. 13/596,266 filed Aug. 28, 2012, which claims priority to U.S. Provisional Application No. 61/529,691 filed Aug. 31, 2011, both herein incorporated by reference in its entirety.

GOVERNMENT SUPPORT

This invention was made with government support under Grant Nos. R01 CA077789, P30 CA023074, and P01 CA056666 awarded by NIH, and under Grant No. W81XWH-12-1-0032 awarded by ARMY. The government has certain rights in the invention.

FIELD

The disclosure provides methods for characterizing a prostate cancer sample by detecting changes in expression of ERG and/or PTEN which are shown herein to be correlated with prostate cancer capsular penetration, biochemical recurrence, and more aggressive forms of prostate cancer. Also provided are kits and arrays that can be used with such methods.

BACKGROUND

Oncologists have a number of treatment options available to them, including different combinations of chemotherapeutic drugs that are characterized as "standard of care," and a number of drugs that do not carry a label claim for particular cancer, but for which there is evidence of efficacy in that cancer. The best chance for a good treatment outcome requires that patients promptly receive optimal available cancer treatment(s) and that such treatment(s) be initiated as quickly as possible following diagnosis. On the other hand, some cancer treatments have significant adverse effects on quality of life; thus, it is equally important that cancer patients do not unnecessarily receive potentially harmful and/or ineffective treatment(s).

Prostate cancer provides a good case in point. In 2008, it was estimated that prostate cancer alone will account for 25% of all cancers in men and will account for 10% of all cancer deaths in men (Jemal et al., *CA Cancer J. Clin.* 58:71-96, 2008). Prostate cancer typically is diagnosed with a digital rectal exam ("DRE") and/or prostate specific antigen (PSA) screening. An abnormal finding on DRE and/or an elevated serum PSA level (e.g., >4 ng/ml) can indicate the presence of prostate cancer. When a PSA or a DRE test is abnormal, a transrectal ultrasound may be used to map the prostate and show any suspicious areas. Biopsies of various sectors of the prostate are used to determine if prostate cancer is present.

The incidence increased with age and the routine availability of serum PSA testing has dramatically increased the number of aging men having the diagnosis. In most men the disease is slowly progressive but a significant number progress to metastatic disease which in time becomes androgen independent. Prognosis is good if the diagnosis is made when the cancer is still localized to the prostate; but nearly one-third of prostate cancers are diagnosed after the tumor has spread locally, and in 1 of 10 cases, the disease has distant metastases at diagnosis. The 5-year survival rate for men with advanced prostate cancer is only 33.6%. The choice of appropriate treatment is usually dependent on the age of the patient and the stage of the prostate cancer. This decision is complicated by the lack of available accurate methods to pre-surgically determine the clinical stage and the biologic potential of a given patient.

An important clinical question is how aggressively to treat such patients with prostate cancer. Usual treatment options depend on the stage of the prostate cancer. Men with a 10-year life expectancy or less who have a low Gleason number and whose tumor has not spread beyond the prostate often are not treated. Treatment options for more aggressive cancers include radical prostatectomy and/or radiation therapy. Androgen-depletion therapy (such as, gonadotropin-releasing hormone agonists (e.g., leuprolide, goserelin, etc.) and/or bilateral orchiectomy) is also used, alone or in conjunction with surgery or radiation. However, these prognostic indicators do not accurately predict clinical outcome for individual patients. Hence, understanding of the molecular abnormalities that define those tumors at high risk for relapse is needed to help identify more precise molecular markers.

Nevertheless a few genes have emerged including hepsin (HPN) (Rhodes et al., *Cancer Res.* 62:4427-33, 2002), alpha-methylacyl-CoA racemase (AMACR) (Rubin et al., *JAMA* 287:1662-70, 2002), and enhancer of Zeste homolog 2 (EZH2) (Varambally et al., *Nature* 419:624-9, 2002), which have been shown experimentally to have probable roles on prostate carcinogenesis. Most recently, bioinformatics approaches and gene expression methods were used to identify fusion of the androgen-regulated transmembrane protease, serine 2 (TMPRSS2) with members of the erythroblast transformation specific (ETS) DNA transcription factors family (Tomlins et al., *Science* 310:644-8, 2005).

Another factor impacting clinical utility of the various proposed panels is the fact that most samples available for validation exist only as formalin fixed paraffin embedded (FFPE) tissues. In contrast, many of the cDNA microarray studies conducted to date typically use snap frozen tissues (Bibikova et al., *Genomics* 89:666-72, 2007; van't Veer et al., *Nature* 415:530-6, 2002). The ability to perform and analyze gene expression in FFPE tissues will greatly accelerate research by correlating already available clinical information such as histological grade and clinical stage with gene specific signatures.

Given that some prostate cancers need not be treated while others almost always are fatal and further given that the disease treatment can be unpleasant at best, there is a strong need for methods that allow care givers to predict the expected course of disease, including the likelihood of cancer recurrence, long-term survival of the patient, and the like, and to select the most appropriate treatment option accordingly.

SUMMARY

It is disclosed herein that increased ERG expression and decreased PTEN expression (or even absence of detectable PTEN expression) is associated with capsular penetration by prostate cancers. For example, detection of increased ERG expression and decreased PTEN expression is correlated with prostate cancer capsular penetration, and in samples from a prostate cancer that has penetrated the capsule (referred to herein as a CP prostate sample), detection of increased ERG expression and decreased PTEN expression is indicative of a more aggressive prostate cancer, such as one likely to biochemically recur. Thus, expression of PTEN and ERG (or even PTEN alone) can be used to forecast prostate cancer outcome (e.g., biochemically recurrence or non-recurrence), for example in patients who have a prostate cancer that has penetrated the capsule. In particular examples, increased ERG expression and decreased PTEN expression indicates an increased likelihood that the prostate cancer is more aggressive and may recur or metastasize, and thus a poor prognosis. The disclosed methods are useful, for example, to screen prostate cancer patients for cancer aggressiveness, which can aid prognosis and the making of therapeutic decisions in prostate cancer. For example, patients identified as having increased ERG expression and decreased PTEN expression in their prostate cancer sample can be selected for more aggressive therapies and/or more frequent monitoring, while patients identified as not having increased ERG expression and decreased PTEN expression in their prostate cancer sample can be selected for less aggressive therapies and/or less frequent monitoring. Methods and compositions (including kits and arrays that include antibodies or probes that specifically bind to ERG and PTEN) that embody this discovery are described.

Methods are provided for characterizing a prostate cancer. Such methods can include detecting or measuring expression of ERG, PTEN, or both in a prostate cancer sample from a subject, such as a CP prostate cancer sample. The expression of ERG and PTEN in the prostate cancer sample is compared to a control representing ERG and PTEN expression expected in a normal prostate sample (e.g., ERG− and PTEN+) and diagnosing or prognosing that the prostate cancer is more aggressive when increased expression of ERG and decreased expression of PTEN is detected in the prostate cancer sample relative to the control. For example, a more aggressive prostate cancer can be one which is more likely to biochemically recur, metastasize, less likely to respond to treatment, or combinations thereof, such as an increased likelihood that the prostate cancer will biochemically recur following prostatectomy within 1, 3, or 5 years.

In addition, kits that include one or more means for detecting in a biological sample an ERG genomic sequence, ERG transcript ERG protein, PTEN genomic sequence, PTEN transcript or PTEN protein, or any combination of any of the foregoing, are provided.

The foregoing and other objects and features of the disclosure will become more apparent from the following detailed description, which proceeds with reference to the accompanying figures.

SEQUENCE LISTING

Figure 1:
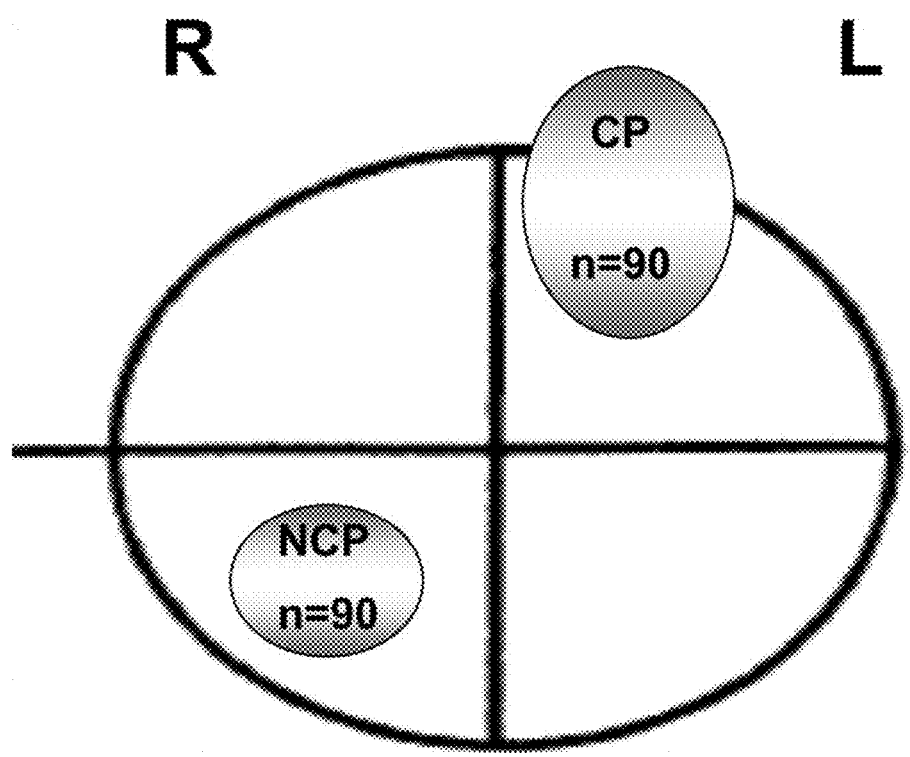
FIG. 1 is a diagram showing the types of prostate tumors analyzed, those having capsular penetration (CP) and those that do not invade the prostatic capsule (NCP).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the filing date of this application. The Sequence Listing is submitted as an ASCII text file, created on Jul. 26, 2016 24 KB, which is incorporated by reference herein. In the accompanying sequence listing:

SEQ ID NOS: 1 and 2 are a human Ets related gene (ERG) nucleic acid coding sequence and corresponding protein sequence.

SEQ ID NOS: 3 and 4 are a human phosphatase and tensin homolog (PTEN) nucleic acid coding sequence and corresponding protein sequence.

SEQ ID NOS: 5 and 6 are primers that can be used to amplify ERG.

SEQ ID NOS: 7 and 8 are primers that can be used to amplify ERG.

SEQ ID NOS: 9 and 10 are primers that can be used to amplify PTEN.

SEQ ID NO: 11 is a CEN10 specific probe.

DETAILED DESCRIPTION

I. Terms

Unless otherwise explained, all technical and scientific terms used herein have the same meaning as commonly understood by one of ordinary skill in the art to which a disclosed invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B."

Suitable methods and materials for the practice and/or testing of embodiments of the disclosed methods are described below. Such methods and materials are illustrative only and are not intended to be limiting. Other methods and materials similar or equivalent to those described herein also can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All sequences associated with the GenBank® accession numbers referenced herein are incorporated by reference (e.g., the sequence present on Aug. 31, 2011 is incorporated by reference).

In order to facilitate review of the various disclosed embodiments, the following explanations of specific terms are provided:

Amplification of a nucleic acid molecule: Refers to methods used to increase the number of copies of a nucleic acid molecule, such as an ERG or PTEN nucleic acid molecule. The resulting products can be referred to as amplicons or amplification products. Methods of amplifying nucleic acid molecules are known in the art, and include MDA, PCR (such as RT-PCR and qRT-PCR), DOP-PCR, RCA, T7/Primase-dependent amplification, SDA, 3SR, NASBA, and LAMP, among others.

Antibody: A polypeptide ligand including at least a light chain or heavy chain immunoglobulin variable region which specifically recognizes and binds an epitope of an antigen, such as an endothelial marker or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody specifically binds to an ERG or PTEN protein, but not other proteins (such as other proteins found in human prostate tissue or that are associated with prostate cancer such as prostate-specific antigen, PSA). Thus, the disclosure provides antibodies that specifically bind to an ERG or PTEN protein, such as a monoclonal or polyclonal antibody specific for ERG or PTEN, such as a labeled monoclonal or polyclonal antibody.

This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. For example, an antibody that binds ERG or PTEN will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an endothelial marker.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Binding affinity: Affinity of one molecule for another, such as an antibody for an antigen (for example, an ERG or PTEN protein). In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1 \times 10^{-8}$M. In other examples, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Capsular penetration or invasion: When referring to a prostate cancer, refers to when prostate cancer extends into and in some examples through the prostatic capsule.

Cancer: Malignant neoplasm, for example one that has undergone characteristic anaplasia with loss of differentiation, increased rate of growth, invasion of surrounding tissue, and is capable of metastasis.

Complementary: A nucleic acid molecule is said to be "complementary" with another nucleic acid molecule if the two molecules share a sufficient number of complementary nucleotides to form a stable duplex or triplex when the strands bind (hybridize) to each other, for example by forming Watson-Crick, Hoogsteen or reverse Hoogsteen base pairs. Stable binding occurs when a nucleic acid molecule (e.g., nucleic acid probe or primer) remains detectably bound to a target nucleic acid sequence (e.g., ERG or PTEN target nucleic acid sequence) under the required conditions.

Complementarity is the degree to which bases in one nucleic acid molecule (e.g., nucleic acid probe or primer) base pair with the bases in a second nucleic acid molecule (e.g., target nucleic acid sequence, such as ERG or PTEN). Complementarity is conveniently described by percentage, that is, the proportion of nucleotides that form base pairs between two molecules or within a specific region or domain of two molecules. For example, if 10 nucleotides of a 15 contiguous nucleotide region of a nucleic acid probe or primer form base pairs with a target nucleic acid molecule, that region of the probe or primer is said to have 66.67% complementarity to the target nucleic acid molecule.

In the present disclosure, "sufficient complementarity" means that a sufficient number of base pairs exist between one nucleic acid molecule or region thereof (such as a region of a probe or primer) and a target nucleic acid sequence (e.g., a ERG or PTEN nucleic acid sequence) to achieve detectable binding. A thorough treatment of the qualitative and quantitative considerations involved in establishing binding conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Contact: To bring one agent into close proximity to another agent, thereby permitting the agents to interact. For example, an antibody (or other specific binding agent) can be applied to a microscope slide or other surface containing a biological sample, thereby permitting detection of proteins (or protein-protein interactions or protein-nucleic acid interactions) in the sample that are specific for the antibody. In another example, a oligonucleotide probe or primer (or other nucleic acid binding agent) can be incubated with nucleic acid molecules obtained from a biological sample (and in some examples under conditions that permit amplification of the nucleic acid molecule), thereby permitting detection of nucleic acid molecules (or nucleic acid-nucleic acid interactions) in the sample that have sufficient complementarity to the probe or primer.

Control: A sample or standard used for comparison with a test sample, such as a biological sample, e.g., a biological sample obtained from a patient (or plurality of patients) or a cell culture. In some embodiments, the control is a sample obtained from a healthy patient (or plurality of patients) (also referred to herein as a "normal" control), such as a normal sample (e.g., one that does not have prostate cancer, such as a normal prostate sample). In some embodiments, the control is a historical control or standard value (i.e., a previously tested control sample or group of samples that represent baseline or normal values). In some embodiments the control is a standard value representing the average value (or average range of values) obtained from a plurality of patient samples. In some examples, the control is ERG expression in endothelial cells and/or PTEN expression in a normal prostate gland.

A control can also be represented by a reference value or range of values representing an amount of activity or expression determined to be representative of a given condition. Reference values can include a range of values, real or relative expected to occur under certain conditions. These values can be compared with experimental values to determine if a given molecule is up-regulated or down-regulated in a particular sample for instance. In one example, a reference value or range of values represents an amount of activity or expression of ERG and/or PTEN proteins and/or nucleic acids in a sample, such as a sample from a subject without prostate cancer (such as a healthy male prostate sample), or non-cancerous tissue adjacent to the prostate cancer in from the same or other patients. This value can then be used to determine if the subject from whom a test sample was obtained has a more aggressive form of prostate cancer by comparing this reference value of expression to the level of expression detected in the test sample. In a particular example, a decrease in PTEN and an increase in ERG expression or activity in a test sample as compared to a reference value for an ERG−/PTEN+ prostate sample indicates that the subject has a more aggressive prostate cancer.

Detect: To determine if an agent (e.g., a nucleic acid molecule or protein) or interaction (e.g., binding between two proteins, between a protein and a nucleic acid, or between two nucleic acid molecules) is present or absent in a sample, for example by making measurements from a sample. In some examples this can further include quantification. In particular examples, an emission signal from a label is detected. Detection can be in bulk, so that a macroscopic number of molecules can be observed simultaneously. Detection can also include identification of signals from single molecules using microscopy and such techniques as total internal reflection to reduce background noise.

For example, use of an antibody specific for a particular protein (e.g., ERG or PTEN) permits detection of the of the protein or protein-protein interaction in a sample, such as a sample containing prostate cancer tissue. In another example, use of a probe or primer specific for a particular gene (e.g., ERG or PTEN) permits detection of the desired nucleic acid molecule in a sample, such as a sample containing prostate cancer tissue.

Diagnose: The process of identifying a medical condition or disease, for example from the results of one or more diagnostic procedures. In one example, the disclosed methods allow for diagnosis of a prostate cancer that has penetrated the prostatic capsule if elevated ERG and decreased PTEN is detected (as compared to expected levels of ERG and PTEN in a normal sample).

Differential Expression: A nucleic acid sequence is differentially expressed when the amount of one or more of its expression products (e.g., transcript (e.g., mRNA) and/or protein) is higher or lower in one tissue (or cell) type as compared to another tissue (or cell) type. Detecting differential expression can include measuring a change in gene or protein expression, such as a change in ERG and PTEN expression. For example, a gene, e.g., ERG, the transcript or protein of which is more highly expressed in a more aggressive prostate cancer tissue (or cells) that has penetrated the prostatic capsule and less expressed in a less aggressive prostate cancer tissue (or cells) that has penetrated the prostatic capsule, is differentially expressed. In another example, a gene, e.g., PTEN, the transcript or protein of which is less expressed (or even not expressed) in a more aggressive prostate cancer tissue (or cells) that has penetrated the prostatic capsule and more greatly expressed in a less aggressive prostate cancer tissue (or cells) that has penetrated the prostatic capsule, is differentially expressed.

Downregulated or inactivation: When used in reference to the expression of a nucleic acid molecule (such as PTEN), such as a gene, refers to any process which results in a decrease or elimination in production of a gene product, such as a PTEN protein. A gene product can be RNA (such as mRNA, rRNA, tRNA, and structural RNA) or protein. Therefore, downregulation or deactivation includes processes that decrease or even eliminate transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Downregulation includes any detectable decrease in the production of a gene product. In certain examples, production of a gene product decreases by at least 2-fold, at least 3-fold, at least 4-fold, at least 5-fold, at least 10-fold, or at least 20-fold (or even not detectable) as compared to a control (such an amount of protein or nucleic acid expression detected in a normal prostate cell). For example PTEN nucleic acids and proteins are more likely downregulated in subjects who have aggressive forms of prostate cancer with capsular penetration, such as a prostate cancer likely to biochemically recur following prostatectomy. In one example, a control is a relative amount of gene expression or protein expression in a prostate sample from a subject (or population of subjects) who does not have prostate cancer.

Expression: The process by which the coded information of a gene is converted into an operational, non-operational, or structural part of a cell, such as the synthesis of a protein. Gene expression can be influenced by external signals (such as a hormone). Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of an ERG or PTEN nucleic acid molecule or protein can be altered relative to a normal (wild type) nucleic acid molecule or protein (such as in a patient not having prostate cancer or has a prostate cancer that has not penetrated the capsule). Alterations in gene expression, such as differential expression, include but are not limited to: (1) overexpression (e.g., upregulation); (2) underexpression (e.g., downregulation); or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount (e.g., upregulation); (5) expression of a decreased amount of the protein compared to a control or standard amount (e.g., downregulation); (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have prostate cancer) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Gene: A nucleic acid (e.g., genomic DNA, cDNA, or RNA) sequence that comprises coding sequences necessary for the production of a polypeptide, precursor, or RNA (e.g., mRNA). The polypeptide can be encoded by a full-length coding sequence or by any portion of the coding sequence so long as the desired activity or functional properties (e.g., enzymatic activity, ligand binding, signal transduction, immunogenicity, etc.) of the full-length or fragment is/are retained. The term also encompasses the coding region of a structural gene and the sequences located adjacent to the coding region on both the 5' and 3' ends for a distance of about 1 kb or more on either end such that the gene corresponds to the full-length mRNA. Sequences located 5' of the coding region and present on the mRNA are referred to as 5' untranslated sequences. Sequences located 3' or downstream of the coding region and present on the mRNA are referred to as 3' untranslated sequences. The gene as present in (or isolated from) a genome contains the coding regions ("exons") interrupted with non-coding sequences termed "introns." Introns are absent in the processed RNA (e.g., mRNA) transcript.

Label: An agent capable of detection, for example by spectrophotometry, flow cytometry, or microscopy. For example, one or more labels can be attached to an antibody, thereby permitting detection of a target protein (such as ERG or PTEN). Furthermore, one or more labels can be attached to a nucleic acid molecule, thereby permitting detection of a target nucleic acid molecule (such as ERG or PTEN DNA or RNA). Exemplary labels include radioactive isotopes, fluorophores, chromophores, ligands, chemiluminescent agents, enzymes, and combinations thereof.

Normal cells or tissue: Non-tumor, non-malignant cells and tissue.

Prognose: The process of determining the likely outcome of a subject having a disease (e.g., prostate cancer) in the absence of additional therapy. In one example, the disclosed methods allow for prognosis of future events, such as the likely biochemical recurrence of prostate cancer after prostatectomy (e.g., likelihood of biochemical recurrence in 1 year, 3 years or 5 years) after pro statectomy, and/or predicting the likely metastasis of a prostate cancer (e.g., after prostatectomy).

Specific binding (or derivations of such phrase, such as specifically binds, specific for, etc.): The particular interaction between one binding partner (such as a gene-specific probe or protein-specific antibody) and another binding partner (such as a target of a gene-specific probe or protein-specific antibody). Such interaction is mediated by one or, typically, more non-covalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a probe-mRNA or antibody-protein interaction) can be competitively removed (or displaced) from such association by excess amounts of either specific binding partner. Such competition assays (or displacement assays) are very well known in the art.

Subject: Includes any multi-cellular vertebrate organism, such as human and non-human mammals (e.g., veterinary subjects). In some examples, a subject is one who has cancer, or is suspected of having cancer, such as prostate cancer, such as a prostate cancer with capsular penetration.

Upregulated or activation: When used in reference to the expression of a molecule, such as a gene or protein, refers to any process which results in an increase in production of a gene product. A gene product can be RNA (such as mRNA, rRNA, tRNA, and structural RNA) or protein. Therefore, upregulation or activation includes processes that increase the presence of ERG proteins or nucleic acids, for example fusions between ERG and TMPRSS resulting in TMPRSS/ERG rearrangements.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Upregulation can include inhibition of repression as well as stimulation of expression above an existing level. Examples of processes that increase translation include those that increase translational initiation, those that increase translational elongation and those that increase mRNA stability.

Upregulation includes any detectable increase in the production of a gene product, such as an ERG protein. In certain examples, detectable ERG protein or nucleic acid expression in an aggressive prostate cancer that has penetrated the capsule increases by at least 2-fold, at least 3-fold, at least 4-fold, at least 5-fold, at least 6-fold, at least 7-fold, at least 8-fold, at least 9-fold, or at least 10-fold as compared to a control (such an amount of detectable ERG protein or nucleic acid in a normal sample). For example ERG is upregulated in subjects who have or a more likely to have an aggressive prostate cancer that has penetrated the capsule. In one example, a control is a relative amount of expression in a normal sample.

II. ERG and PTEN Expression Correlate with Capsular Penetration in Prostate Cancer It is disclosed herein that increased expression of ERG and decreased or even eliminated expression of PTEN, relative to such expression in normal prostate tissues (e.g., an ERG−/PTEN+ prostate sample), are predictive of increased risk of capsular penetration in prostate cancers, more aggressive prostate cancer, increased likelihood of biochemical recurrence, and poor prognosis. In some examples, decreased or even eliminated expression of PTEN, relative to such expression in normal prostate tissues (e.g., an ERG−/PTEN+ prostate sample), are predictive of increased likelihood of prostate cancer biochemical recurrence following prostatectomy. Methods and compositions that embody this discovery are described.

Provided herein are methods of characterizing a prostate cancer, such as a prostate cancer that has penetrated the prostatic capsule. In particular examples, the method is diagnostic, in that it determines that a prostate cancer has penetrated the prostatic capsule. In particular examples, the method is prognostic, in that it predicts the likelihood that the prostate cancer will penetrate the prostatic capsule. In other examples, the method is prognostic, in that it predicts whether the prostate cancer is likely to or biochemically recur (for example after prostatectomy). Biochemical recurrence (BCR) is any detectable prostate specific antigen (PSA) after prostatectomy or a PSA rise after a period of PSA detection absence (see Simmons et al., *Eur. Urol.* 51:1175-84, 2007). After prostatectomy, PSA levels typically decrease to an undetectable level after about four weeks. In some examples, BCR is indicated by PSA levels ≥0.2 ng/ml, such as ≥0.4 ng/ml or ≥0.2 to 0.6 ng/ml, such as two successive PDS levels ≥0.2 ng/ml or ≥0.4 ng/ml, following prostatectomy. BCR is indicative of the presence of prostatic epithelial tissue, and is assumed to represent cancer.

The sample can be a fixed, wax-embedded prostate cancer tissue sample, such as a fixed, wax-embedded prostate cancer tissue sample, which has or has not penetrated the capsule. In some examples, the prostate cancer sample is collected after prostate cancer diagnosis and after prostatectomy in the subject, or can be collected during a prostatectomy. In some examples, the prostate cancer sample is a prostate cancer that has penetrated the prostatic capsule. In other examples, the sample is obtained during a prostate tissue biopsy of a tumor suspected or known to be cancerous or suspected or known to have penetrated the capsule.

In particular methods, the method includes detecting or measuring expression of ERG, PTEN, or both in a prostate cancer sample from a subject (for example determining ERG and PTEN expression levels qualitatively or quantitatively). The expression of ERG and PTEN can be detected at the genomic level, or gene expression products can be detected, such as ERG and PTEN nucleic acids (e.g., mRNA, cDNA) or proteins. In some examples, determining the expression level includes detecting alteration(s) in the genomic sequence(s) of ERG or PTEN, such as detecting a TMPRSS-ERG rearrangement or PTEN deletion. For example, the method can include detecting amplification of at least one ERG allele, fusion of at least one ERG allele, deletion of at least one PTEN allele, or combinations thereof.

The ERG or PTEN expression, or both, in the test prostate cancer sample are compared to ERG and PTEN expression in a control, such as a control that represents ERG and PTEN expression expected in a normal prostate sample (which are ERG− and PTEN+) or normal endothelial cells. Based on the expression levels of ERG and PTEN in the test sample as compared to the control, the prostate cancer is characterized, such as diagnosed or prognosed. In some examples, the method can include one or more of obtaining the prostate cancer sample (e.g., a sample from a prostate cancer that has penetrated the capsule); fixing the sample; and contacting the sample with ERG and PTEN specific binding agents (e.g., nucleic acid probes or antibodies).

For example, the method can include determining that there is a higher likelihood that the prostate cancer will penetrate the prostatic capsule in the future when increased expression of ERG and decreased expression of PTEN is detected in the prostate cancer sample relative to the normal control. In another example, the method can include determining or diagnosing that the prostate cancer has penetrated the prostatic capsule when increased expression of ERG and decreased expression of PTEN is detected in the prostate cancer sample relative to the normal control. In another example, the method can diagnose that the prostate cancer that has penetrated the prostatic capsule is more aggressive when increased expression of ERG and decreased expression of PTEN is detected in the prostate cancer sample relative to the control. In another example, the method can prognose an increased likelihood that the prostate cancer that has penetrated the prostatic capsule is more aggressive when increased expression of ERG and decreased expression of PTEN is detected in the prostate cancer sample relative to the control. In another example, the method can prognose an increased likelihood that the prostate cancer will biochemically recur when decreased expression of PTEN (in some examples in combination with increased expression of ERG) is detected in the prostate cancer sample relative to the control.

In one example, determining that there is a higher or greater likelihood that the prostate cancer will penetrate the prostatic capsule in the future when increased expression of ERG and decreased expression of PTEN is detected in the prostate cancer sample relative to the normal control (e.g., an ERG−/PTEN+ prostate sample), indicates that the prostate cancer is about 3 times to about 5 times more likely (such as about 4 times to about 5 times, about 4.5 times to about 5 times, or about 3, 4, 4.5, 4.8, 4.9, or 5 times, more likely) to penetrate the prostatic capsule, than a prostate cancer sample that does not have increased expression of ERG and decreased expression of PTEN relative to the control.

In one example, a prognosis that the cancer is more aggressive indicates that the prostate cancer is predicted to biochemically recur within 1 year, within 3 years or within 5 years of a prostatectomy. In one example, a prognosis that the cancer is more aggressive indicates that the prostate cancer is predicted to metastasize within 1 year, within 3 years or within 5 years of a prostatectomy. For example, a prognosis that the cancer is more likely to biochemically recur or metastasize can be relative to a prostate cancer sample that does not have increased expression of ERG and decreased expression of PTEN relative to the control (e.g., an ERG−/PTEN+ prostate sample).

In one example, a prognosis that the cancer is less aggressive (e.g., levels of ERG ad PTEN similar to a normal prostate; that is ERG not significantly upregulated and significant PTEN expression detected) indicates that the prostate cancer is predicted to not biochemically recur within 1 year, within 3 years or within 5 years of a prostatectomy. In one example, a diagnosis or prognosis that the cancer is less aggressive indicates that the prostate cancer is not predicted to metastasize within 1 year, within 3 years or within 5 years of a prostatectomy.

The method can further include detecting or measuring expression of one or more other prostate cancer related molecules in the sample and comparing expression of the one or more other prostate cancer related molecules in the prostate cancer sample to a control representing expression of the one or more other prostate cancer related molecules expected in a normal prostate sample. Prostate cancer related molecules include those whose expression is known to be altered (such as increased or decreased) in a prostate cancer sample, relative to a normal prostate cancer sample. Examples include but are not limited to: growth arrest-specific 1 (GAS1; OMIM 139185), wingless-type MMTV integration site family member 5 (WNT5A; OMIM 164975), thymidine kinase 1 (TK1; OMIM 188300), V-raf murine sarcoma viral oncogene homolog B1 (BRAF; OMIM 164757), ETS translocation variant 4 (ETV4; OMIM 600711), tumor protein p63 (OMIM 603273), BCL-2 (OMIM 151430), Ki67 (OMIM 176741), ERK5 (OMIM 602521), prostate specific antigen (PSA; OMIM 176820), ETS translocation variant 1 (ETV1; OMIM 600541), measures of nuclear morphology (including nuclear size and shape variation characteristics), or combinations thereof.

In some examples, the method can further include detecting expression of one or more control molecules in the sample and comparing expression of the one or more control molecules in the prostate cancer sample to a control representing expression of the one or more control molecules expected in a normal prostate sample. In some examples, expression of ERG and/or PTEN is normalized to expression of one or more internal controls, such as ERG expression in endothelial cells or PTEN expression in a normal gland.

A. Methods of Use

This disclosure identifies ERG and PTEN are differentially expressed in prostate cancer that has penetrated the capsule and more aggressive prostate cancers that have penetrated the capsule. In addition, it is shown that PTEN is down-regulated in prostate cancer that is more likely to biochemically recur following prostatectomy. A more-aggressive prostate cancer can be indicated by recurrence of after treatment (e.g., prostatectomy), a worse prognosis for the patient (e.g., decreased survival time), an increased likelihood of disease progression (e.g., metastasis), failure (or inadequacy) of treatment, and/or a need for alternative (or additional) treatments. Accordingly, the present discoveries have enabled, among other things, a variety of methods for characterizing prostate cancer tissues, diagnosis or prognosis of prostate cancer patients, predicting treatment outcome in prostate cancer patients, and directing (e.g., selecting useful) treatment modalities for prostate cancer patients (such as a patient with a prostate cancer that has penetrated the capsule).

In some examples, the disclosed methods can be used to identify those subjects that will benefit from a more or less aggressive therapy. For example, if a patient is diagnosed or prognosed with an aggressive form of prostate cancer, the patient can be selected for more aggressive treatment and frequent monitoring. In in contrast, if a patient is diagnosed or prognosed with a less aggressive form of prostate cancer, the patient can be selected for less aggressive treatment and less frequent monitoring. Thus in some examples, the disclosed methods further include selecting a patient for more or less aggressive treatment or monitoring, depending on the ERG and PTEN expression detected. For example, such diagnostic or prognostic methods can be performed prior to the subject undergoing the treatment. Thus, the methods of the present disclosure are valuable tools for practicing physicians to make quick treatment decisions regarding how to treat prostate cancer, such as prostate cancer that has penetrated the capsule. These treatment decisions can include the administration of an agent for treating prostate cancer and decisions to monitor a subject for recurrence or metastasis of a prostate cancer that has penetrated the capsule. Thus, in some examples, the disclosed methods further include treating the subject with prostate cancer, for example administering one or more therapeutic agents for treating prostate cancer, such as chemotherapeutics (e.g., temozolomide or docetaxel) or hormone therapy, treating the patient with radiation therapy (e.g., prostate brachytherapy), performing a prostatectomy, or combinations thereof.

Disclosed methods can be performed using biological samples obtained from a subject having prostate cancer, such as a prostate cancer that has or has not invaded the prostatic capsule. A typical subject is a human male; however, any mammal that has a prostate that may develop prostate cancer can serve as a source of a biological sample useful in a disclosed method. Exemplary biological samples useful in a disclosed method include tissue samples (such as prostate biopsies and/or prostatectomy tissues) or prostate cell samples (such as can be collected by prostate massage, in the urine, or in fine needle aspirates). In one example, the sample is a prostate cancer sample that has penetrated the capsular region. Samples may be fresh or processed post-collection (e.g., for archiving purposes). In some examples, processed samples may be fixed (e.g., formalin-fixed) and/or wax-(e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago:ASCP Press, 1997). Particular method embodiments involve FFPE prostate cancer tissue samples. In some examples, the sample (or a fraction thereof) is present on a solid support. Solid supports useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

Exemplary methods involve determining in a prostate tissue sample from a subject the expression level of ERG and PTEN. In some examples, the expression level of additional nucleic acids or proteins are determined, for example one or more other prostate cancer related markers, such as growth arrest-specific 1 (GAS1; OMIM 139185), wingless-type MMTV integration site family member 5 (WNT5A; OMIM 164975), thymidine kinase 1 (TK1; OMIM 188300), V-raf murine sarcoma viral oncogene homolog B1 (BRAF; OMIM 164757), ETS translocation variant 4 (ETV4; OMIM 600711), tumor protein p63 (OMIM 603273), BCL-2 (OMIM 151430), Ki67 (OMIM 176741), ERK5 (OMIM 602521), prostate specific antigen (PSA; OMIM 176820), ETV1 (OMIM 600541), measures of nuclear morphology (including nuclear size and shape variation characteristics) or combinations thereof. In addition, the expression level of one or more control genes can also be determined.

In exemplary methods, expression of ERG is increased and expression of PTEN is decreased as compared to a standard value or a control sample. In other methods, the expression of another gene (e.g., WNT5A, TK1 or PSA) is increased. In some such methods, the relative increased expression of ERG and the relative decreased expression of PTEN indicates, for example, a higher likelihood of prostate cancer progression in the subject (e.g., a higher likelihood that the prostate cancer will invade the capsule in the subject), an increased likelihood that the prostate cancer will biochemically recur after surgery (e.g., prostatectomy), an increased likelihood that the prostate cancer will metastasize after surgery (e.g., prostatectomy), and/or a higher likelihood that surgical treatment (e.g., prostatectomy) will fail, and an increased need for a non-surgical or alternate treatment for the prostate cancer.

In some methods, the expression of one or more genes of interest (e.g., ERG and PTEN) is measured relative to a standard value or a control sample. A standard values can include, without limitation, the average expression of the one or more genes of interest in a normal prostate or endothelial cells (e.g., calculated in an analogous manner to the expression value of the genes in the prostate cancer sample), the average expression of the one or more genes of interest in a prostate sample obtained from a patient or patient population in which it is known that prostate cancer did not invade the capsule, the average expression of the one or more genes of interest in a prostate sample obtained from a region adjacent to the prostate cancer (e.g., normal prostate tissue adjacent to the cancer tissue); or the average expression of the one or more genes of interest in a prostate sample obtained from a patient or patient population in which it is known that prostate cancer did invade the capsule. A control sample can include, for example, normal prostate tissue or cells, prostate tissue or cells collected from a patient or patient population in which it is known that prostate cancer did not invade the capsule, prostate tissue or cells collected from a patient or patient population in which it is known that prostate cancer did invade the capsule, normal endothelial cells and/or endothelial cells collected from a patient or patient population in which it is known that prostate cancer did or did not invade the capsule.

In other methods, expression of the gene(s) of interest is (are) measured in test (i.e., prostate cancer patient sample) and control samples relative to a value obtained for a control gene (e.g., one or more of GAPDH (glyceraldehyde 3-phosphate dehydrogenase), SDHA (succinate dehydrogenase), HPRT1 (hypoxanthine phosphoribosyl transferase 1), HBS1L (HBS1-like protein), β-actin, and AHSP (alpha haemoglobin stabilizing protein)) in each sample to produce normalized test and control values; then, the normalized value of the test sample is compared to the normalized value of the control sample to obtain the relative expression of the gene(s) of interest (e.g., increased expression of ERG and decreased expression of PTEN). In some examples, expression of ERG and/or PTEN is normalized to expression of one or more internal controls, such as ERG expression in endothelial cells or PTEN expression in a normal gland.

An increase or decrease in gene expression may mean, for example, that the expression of a particular gene expression product (e.g., transcript (e.g., mRNA) or protein) in the test sample is at least about 20%, at least about 25%, at least about 30%, at least about 50%, at least about 75%, at least about 100%, at least about 150%, or at least about 200% higher or lower, respectively, of the applicable control (e.g., standard value or control sample). Alternatively, relative expression (i.e., increase or decrease) may be in terms of fold difference; for example, the expression of a particular gene expression product (e.g., transcript (e.g., mRNA) or protein) in the test sample may be at least about 2-fold, at least about 3-fold, at least about 4-fold, at least about 5-fold, at least about 8-fold, at least about 10-fold, at least about 20-fold, at least about 50-fold, at least about 100-fold, or at least about 200-fold times higher or lower, respectively, of the applicable control (e.g., standard value or control sample).

In some method embodiments where protein expression as determined by immunohistochemistry is used as a measure of expression, scoring of protein expression may be semi-quantitative; for example, with protein expression levels recorded as 0, 1, 2, or 3 (including, in some instances plus (or minus) values at each level, e.g., 1+, 2+, 3+) with 0 being substantially no detectable protein expression and 3 (or 3+) being the highest detected protein expression. In such methods, an increase or decrease in the expression is measured as a difference in the score as compared the applicable control (e.g., standard value or control sample); that is, a score of 3+ in a test sample as compared to a score of 0 for the control represents increased expression in the test sample, and a score of 0 in a test sample as compared to a score of 3+ for the control represents decreased expression in the test sample.

Biochemical recurrence means the patient's PSA value has increased prostate after prostatectomy or a PSA rise after a period of PSA detection absence (for example after an initial (or subsequent) treatment(s), such as radiation treatment, chemotherapy, anti-hormone treatment and/or surgery). Typically after an initial prostate cancer treatment PSA levels in the blood decrease to a stable and low level and, in some instances, eventually become almost undetectable. In some examples, recurrence of the prostate cancer is marked by rising PSA levels (e.g., at least 0.2 ng/ml, at least 0.4 ng/ml, at least 0.6 ng/ml, at least 1 ng/ml, or at least 2 ng/ml, or at least 5 ng/ml) and/or by identification of prostate cancer cells in the blood, prostate biopsy or aspirate, in lymph nodes (e.g., in the pelvis or elsewhere) or at a metastatic site (e.g., muscles that help control urination, the rectum, the wall of the pelvis, in bones or other organs).

Other exemplary methods predict the likelihood of prostate progression. Prostate cancer progression means that one or more indices of prostate cancer (e.g., serum PSA levels) show that the disease is advancing independent of treatment. In some examples, prostate cancer progression is marked by rising PSA levels (e.g., greater than 0.2 ng/mL) and/or by identification of (or increasing numbers of) prostate cancer cells in the blood, prostate biopsy or aspirate, in lymph nodes (e.g., in the pelvis or elsewhere) or at a metastatic site (e.g., muscles that help control urination, the rectum, the wall of the pelvis, in bones or other organs).

An increased likelihood of prostate cancer progression or prostate cancer recurrence can be quantified by any known metric. For example, an increased likelihood can mean at least a 10% chance of occurring (such as at least a 25% chance, at least a 50% chance, at least a 60% chance, at least a 75% chance or even greater than an 80% chance of occurring).

Some method embodiments are useful for prostate cancer prognosis, such as prostate cancers that have penetrated the capsule. Prognosis is the likely outcome of the disease (typically independent of treatment). The PTEN expression (in some examples in combination with ERG expression) can be used to predict prostate cancer biochemical recurrence in a sample collected well prior to such recurrence (such as a prostate CP sample). In some method embodiments, an increased likelihood of biochemical recurrence an increased likelihood of biochemical recurrence within 1 year, within 2 years, within 3 year, within 4 years, or within 5 years after prostatectomy (for example as compared to a patient with a prostate cancer that is ERG+/PTEN+ or ERG−/PTEN+). Hence, such gene signature is a surrogate for the aggressiveness of the cancer with recurring cancers being more aggressive. A poor (or poorer) prognosis is likely for a subject with a more aggressive cancer (such as having an increased likelihood of metastasis or biochemical recurrence).

Still other method embodiments predict treatment outcome in prostate cancer patients, and are useful for directing (e.g., selecting useful) treatment modalities for prostate cancer patients, such as prostate cancers that have penetrated the capsule. As discussed elsewhere in this specification, expression of ERG and PTEN can be used to predict that prostate cancer treatment (e.g., prostatectomy) is likely to fail (e.g., the disease will recur). Hence, the disclosed gene signature(s) can be used by caregivers to counsel prostate cancer patients as to the likely success of treatment (e.g., prostatectomy). Taken in the context of the particular subject's medical history, the patient and the caregiver can make better informed decisions of whether or not to treat (e.g., perform surgery, such as prostatectomy) and/or whether or not to provide alternate treatment (such as, external beam radiotherapy, brachytherapy, chemotherapy, or watchful waiting).

1. Determining Expression Level (e.g., Gene Expression Profiling)

Expression levels may be determined or detected using any technique known in the art. Exemplary techniques include, for example, methods based on hybridization analysis of polynucleotides (e.g., genomic nucleic acid sequences and/or transcripts (e.g., mRNA)), methods based on sequencing of polynucleotides, methods based on detecting proteins (e.g., immunohistochemistry and proteomics-based methods). In some examples, expression is measured or determined using a suitably programmed computer or instrumentation (for example using the BenchMark (e.g., BenchMark ULTRA) and/or iScan Coreo Au slide scanner from Ventana). In some examples, expression of PTEN and ERG in the test sample is compared to a control using a suitably programmed computer (for example, PTEN and ERG expression values determined the test sample can be compared to a control value of PTEN and ERG expression expected in a normal prostate sample using a computer).

As discussed previously, gene expression levels may be affected by alterations in the genome (e.g., gene amplification, gene deletion, gene fusion, or other chromosomal rearrangements or chromosome duplications (e.g., polysomy) or loss of one or more chromosomes). Accordingly, in some embodiments, gene expression levels may be inferred or determined by detecting such genomic alterations. Genomic sequences harboring genes of interest may be quantified, for example, by in situ hybridization of gene-specific genomic probes to chromosomes in a metaphase spread or as present in a cell nucleus. The making of gene-specific genomic probes is well known in the art (see, e.g., U.S. Pat. Nos. 5,447,841, 5,756,696, 6,872,817, 6,596,479, 6,500,612, 6,607,877, 6,344,315, 6,475,720, 6,132,961, 7,115,709, 6,280,929, 5,491,224, 5,663,319, 5,776,688, 5,663,319, 5,776,688, 6,277,569, 6,569,626, U.S. patent application Ser. No. 11/849,060, and PCT Appl. No. PCT/US07/77444). In some exemplary methods, quantification of gene amplifications or deletions may be facilitated by comparing the number of binding sites for a gene-specific genomic probe to a control genomic probe (e.g., a genomic probe specific for the centromere of the chromosome upon which the gene of interest is located). In some examples, gene amplification or deletion may be determined by the ratio of the gene-specific genomic probe to a control (e.g., centromeric) probe. For example, a ratio greater than two (such as greater than three, greater than four, greater than five or ten or greater) indicates amplification of the gene (or the chromosomal region) to which the gene-specific probe binds. In another example, a ratio less than one indicates deletion of the gene (or the chromosomal region) to which the gene-specific probe binds. In particular method embodiments, it can be advantageous to also determine that gene amplification (or fusion) or deletion is accompanied by a corresponding increase or decrease, respectively, in the expression products of the gene (e.g., mRNA or protein); however, once a correlation is established, continued co-detection is not needed (and may consume unnecessary resources and time).

Gene expression levels also can be determined by quantification of gene transcript (e.g., mRNA). Commonly used methods known in the art for the quantification of mRNA expression in a sample include, without limitation, northern blotting and in situ hybridization (e.g., Parker and Barnes, *Meth. Mol. Biol.*, 106:247-283, 1999)); RNAse protection assays (e.g., Hod, *Biotechniques*, 13:852-854, 1992); and PCR-based methods, such as reverse transcription polymerase chain reaction (RT-PCR) (Weis et al., *Trends in Genetics*, 8:263-264, 1992) and real time quantitative PCR, also referred to as qRT-PCR). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), and gene expression analysis by massively parallel signature sequencing (MPSS).

Some method embodiments involving the determination of mRNA levels utilize RNA (e.g., total RNA) isolated from a target sample, such a prostate cancer tissue sample. General methods for RNA (e.g., total RNA) isolation are well known in the art and are disclosed in standard textbooks of molecular biology, including Ausubel et al., *Current Protocols of Molecular Biology*, John Wiley and Sons (1997). Methods for RNA extraction from paraffin-embedded tissues are disclosed in Examples herein and, for example, by Rupp and Locker (*Lab. Invest.,* 56:A67, 1987) and DeAndres et al. (*BioTechniques,* 18:42044, 1995). In particular examples, RNA isolation can be performed using a purification kit, buffer set and protease obtained from commercial manufacturers, such as Qiagen, according to the manufacturer's instructions. Other commercially available RNA isolation kits include MASTERPURE™ Complete DNA and RNA Purification Kit (EPICENTRE™ Biotechnologies) and Paraffin Block RNA Isolation Kit (Ambion, Inc.).

In the MassARRAY™ gene expression profiling method (Sequenom, Inc.), cDNA obtained from reverse transcription of total RNA is spiked with a synthetic DNA molecule (competitor), which matches the targeted cDNA region in all positions, except a single base, and serves as an internal standard. The cDNA/competitor mixture is amplified by standard PCR and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight (MALDI-TOF) mass spectrometry analysis. The cDNA present in the reaction is then quantified by analyzing the ratios of the peak areas in the mass spectrum generated. For further details see, e.g., Ding and Cantor, *Proc. Natl. Acad. Sci. USA,* 100:3059-3064, 2003.

Other methods for determining mRNA expression that involve PCR include, for example, differential display (Liang and Pardee, *Science,* 257:967-971, 1992)); amplified fragment length polymorphism (Kawamoto et al., *Genome Res.,* 12:1305-1312, 1999); BEADARRAY™ technology (Illumina, San Diego, Calif., USA; Oliphant et al., *Discovery of Markers for Disease* (Supplement to *Biotechniques*), June 2002; Ferguson et al., *Anal. Chem.,* 72:5618, 2000; and Examples herein); XMAP™ technology (Luminex Corp., Austin, Tex., USA); BADGE assay (Yang et al., *Genome Res.,* 11:1888-1898, 2001)); and high-coverage expression profiling (HiCEP) analysis (Fukumura et al., *Nucl. Acids. Res.,* 31(16):e94, 2003).

Differential gene expression also can be determined using microarray techniques. In these methods, specific binding partners, such as probes (including cDNAs or oligonucleotides) specific for RNAs of interest or antibodies specific for proteins of interest are plated, or arrayed, on a microchip substrate. The microarray is contacted with a sample containing one or more targets (e.g., mRNA or protein) for one or more of the specific binding partners on the microarray. The arrayed specific binding partners form specific detectable interactions (e.g., hybridized or specifically bind to) their cognate targets in the sample of interest.

Serial analysis of gene expression (SAGE) is a method that allows the simultaneous and quantitative analysis of a large number of gene transcripts, without the need of providing an individual hybridization probe for each transcript. In the SAGE method, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantified by determining the abundance of individual tags, and identifying the gene corresponding to each tag (see, e.g., Velculescu et al., *Science*, 270:484-487, 1995, and Velculescu et al., *Cell*, 88:243-51, 1997).

Gene expression analysis by massively parallel signature sequencing (MPSS) was first described by Brenner et al. (*Nature Biotechnology*, 18:630-634, 2000). It is a sequencing approach that combines non-gel-based signature sequencing with in vitro cloning of millions of templates on separate 5 µm diameter microbeads. A microbead library of DNA templates is constructed by in vitro cloning. This is followed by the assembly of a planar array of the template-containing microbeads in a flow cell at a high density. The free ends of the cloned templates on each microbead are analyzed simultaneously using a fluorescence-based signature sequencing method that does not require DNA fragment separation.

In some examples, differential gene expression is determined using in situ hybridization techniques, such as fluorescence in situ hybridization (FISH) or chromogen in situ hybridization (CISH). In these methods, specific binding partners, such as probes labeled with a flouurphore or chromogen specific for a target gene, cDNA or mRNA (e.g., a ERG or PTEN gene) is contacted with a sample, such as a prostate cancer sample mounted on a substrate (e.g., glass slide). The specific binding partners form specific detectable interactions (e.g., hybridized to) their cognate targets in the sample. For example, hybridization between the probes and the target nucleic acid can be detected, for example by detecting a label associated with the probe. In some examples, microscopy, such as fluorescence microscopy, is used.

Immunohistochemistry (IHC) is one exemplary technique useful for detecting protein expression products in the disclosed methods. Antibodies (e.g., monoclonal and/or polyclonal antibodies) specific for each protein are used to detect expression. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, unlabeled primary antibody is used in conjunction with a labeled secondary antibody, comprising antisera, polyclonal antisera or a monoclonal antibody specific for the primary antibody. IHC protocols and kits are well known in the art and are commercially available.

Proteomic analysis is another exemplary technique useful for detecting protein expression products in the disclosed methods. The term "proteome" is defined as the totality of the proteins present in a sample (e.g., tissue, organism, or cell culture) at a certain point of time. Proteomics includes, among other things, study of the global changes of protein expression in a sample (also referred to as "expression proteomics"). An exemplary proteomics assay involves (i) separation of individual proteins in a sample, e.g., by 2-D gel electrophoresis; (ii) identification of the individual proteins recovered from the gel, e.g., by mass spectrometry or N-terminal sequencing, and (iii) analysis of the data.

2. Outputting Expression Level

Following the measurement of the expression levels of one or more of the molecules described herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of ERG or PTEN (or in combination with other diagnostics, such as those on a prostate cancer nomogram, such as PSA value and Gleason grade) is communicated to interested parties as soon as possible after the assay is completed and the diagnosis and/or prediction is generated. The results and/or related information may be communicated to the subject by the subject's treating physician. Alternatively, the results may be communicated directly to interested parties by any means of communication, including writing, such as by providing a written report, electronic forms of communication, such as email, or telephone. Communication may be facilitated by use of a suitably programmed computer, such as in case of email communications. In certain embodiments, the communication containing results of a diagnostic test and/or conclusions drawn from and/or treatment recommendations based on the test, may be generated and delivered automatically to interested parties using a combination of computer hardware and software which will be familiar to artisans skilled in telecommunications. One example of a healthcare-oriented communications system is described in U.S. Pat. No. 6,283, 761; however, the present disclosure is not limited to methods which utilize this particular communications system. In certain embodiments of the methods of the disclosure, all or some of the method steps, including the assaying of samples, diagnosing or prognosis of prostate cancer, and communicating of assay results or diagnoses or prognosis, may be carried out in diverse (e.g., foreign) jurisdictions.

B. Capsular Penetration Biomarkers

1. Ets Related Gene (ERG) (OMIM: 165080)

The human Ets related gene (ERG) (also known as erg-3 and p55) is located on chromosome 21 (21q22.3) and is a member of the ETS family of transcription factors. ERG sequences are publically available, for example from GenBank® (e.g., accession numbers NP_001129626 and NP_598420.1 (proteins) and NM_133659.2, NM_001136154.1, and NM_001838708.2 (nucleic acids)).

ERG protein (see, e.g., SEQ ID NO: 2) is a transcriptional regulator that binds purine-rich sequences. Fusion of the ERG gene with other genes has been shown to be associated with different cancers. For example, the t(16;21)(p11;q22) translocation of the ERG gene fused with the fused in sarcoma (FUS) gene is associated with human myeloid leukemia. EWS-ERG fusions are associated with the Ewing family of tumors. ERG fusion with the 5' untranslated region of transmembrane protease, serine 2 (TMPRSS2) (located on human chromosome 21) are associated with prostate cancer. The TMPRS22 and ERG genes are arranged tandemly on chromosome 21q22. The TMPRSS2/ERG fusion joins TMPRSS2 exons 1 or 2 usually to ERG exons 2, 3 or 4, which results in activation of the ERG transcription factor. TMPRSS/ERG rearrangements occur in about 50% of prostate cancers and 20% of high-grade prostatic intraepithelial neoplasia (HGPIN) lesions, resulting in upregulation of ERG. TMPRSS/ERG rearrangement results in a PIN like lesion which can be converted to an invasive state by up-regulation of the PI3K pathway.

between different organisms. In particular examples, a variant sequence retains the biological activity of its corresponding native sequence. For example, a ERG or PTEN sequence present in a particular subject may can have conservative amino acid changes (such as, very highly conserved substitutions, highly conserved substitutions or conserved substitutions), such as 1 to 5 or 1 to 10 conservative amino acid substitutions. Exemplary conservative amino acid substitutions are shown in Table 1.

TABLE 1

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

2. Phosphatase and Tensin Homolog (PTEN) (OMIM 601728)

The human PTEN gene is located on chromosome 10 and the mouse PTEN gene is located on chromosome 19. PTEN sequences (both wild-type and mutant) are publically available, for example from GenBank® (e.g., accession numbers NP_000305.3, AAD13528.1, EAW50174.1, EAW50173.1, EAW50172.1, AAH05821.1 and NP_032986.1 (proteins) and NM_000314.4 and NM_008960.2 (nucleic acids)).

PTEN, also referred to as MMAC (mutated in multiple advanced cancers) phosphatase, is a tumor suppressor gene implicated in a wide variety of human cancers. The PTEN protein (e.g., SEQ ID NO: 4) is a phosphatidylinositol-3,4,5-trisphosphate 3-phosphatase, which includes a tensin-like domain as well as a catalytic domain. Unlike most protein tyrosine phosphatases, PTEN preferentially dephosphorylates phosphoinositide substrates. PTEN negatively regulates intracellular levels of phosphatidylinositol-3, 4, 5-trisphosphate in cells and functions as a tumor suppressor by negatively regulating Akt/PKB signaling pathway. Mutations and deletions of PTEN have been shown to be associated with cancers.

3. Variant Sequences

In addition to the specific sequences provided herein (e.g., SEQ ID NOS: 1-4), and the sequences which are currently publically available, one skilled in the art will appreciate that variants of such sequences may be present in a particular subject. For example, polymorphisms for a particular gene or protein may be present. In addition, a sequence may vary In some embodiments, an ERG or PTEN sequence is a sequence variant of a native ERG or PTEN sequence, respectively, such as a nucleic acid or protein sequence that has at least 99%, at least 98%, at least 95%, at least 92%, at least 90%, at least 85%, at least 80%, at least 75%, at least 70%, at least 65%, or at least 60% sequence identity to the sequences set forth in SEQ ID NOS: 1-4 (or such amount of sequence identity to a GenBank® accession number referred to herein) wherein the resulting variant retains ERG or PTEN biological activity. "Sequence identity" is a phrase commonly used to describe the similarity between two amino acid sequences (or between two nucleic acid sequences). Sequence identity typically is expressed in terms of percentage identity; the higher the percentage, the more similar the two sequences.

Methods for aligning sequences for comparison and determining sequence identity are well known in the art. Various programs and alignment algorithms are described in: Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA*, 85:2444, 1988; Higgins and Sharp, *Gene*, 73:237-244, 1988; Higgins and Sharp, *CABIOS*, 5:151-153, 1989; Corpet et al., *Nucleic Acids Research*, 16:10881-10890, 1988; Huang, et al., *Computer Applications in the Biosciences*, 8:155-165, 1992; Pearson et al., *Methods in Molecular Biology*, 24:307-331, 1994; Tatiana et al., *FEMS Microbiol. Lett.*, 174:247-250, 1999. Altschul et al. present a detailed consideration of sequence-alignment methods and homology calculations (*J. Mol. Biol.*, 215:403-410, 1990).

The National Center for Biotechnology Information (NCBI) Basic Local Alignment Search Tool (BLAST™, Altschul et al., *J. Mol. Biol.*, 215:403-410, 1990) is publicly available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 15 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=3]; reward for a match [default=1]; expectation value (E) [default=10.0]; word size [default=3]; and number of one-line descriptions (V) [default=100]. When aligning short peptides (fewer than around 15 amino acids), the alignment should be performed using the Blast 2 sequences function "Search for short nearly exact matches" employing the PAM30 matrix set to default parameters (expect threshold=20000, word size=2, gap costs: existence=9 and extension=1) using composition-based statistics.

C. Use in Combination with Other Diagnostic and Prognostic Assays

The disclosed methods can be used in combination with one or more other assays that are used to diagnose or prognose prostate cancer outcomes. For example, a prostate cancer patient's Gleason scores based on a histopathological review, PSA scores, and nomograms (such as the Partin Coefficient Tables) can be used in combination with the disclosed methods to allow for enhanced diagnostic and prognostic capabilities of prostate cancer, such as those that have penetrated the capsule. Thus, in some examples, the disclosed methods further include measuring the patient's PSA level, determining the patient's nomogram, or both.

For example, prostate cancer nomograms can be used to predict the probability that a patient's cancer will recur (for example after radical prostatectomy), that is, the probability at one, two, five, seven and 10 years that the patient's serum PSA level will become detectable and begin to rise steadily. Nomograms include information on one or more of the patient's pre-treatment PSA, age, Gleason grade (primary, secondary and sum), year of prostatectomy, months free of cancer, whether or not the surgical margins were positive, whether or not there was extra capsular extension (penetration); whether or not there was seminal vesicle involvement, whether or not there was lymph node involvement, whether or not the patient receive neoadjuvant hormones, and whether whether or not the patient receive radiation therapy before the radical prostatectomy. Thus, the patient's ERG and PTEN expression levels can be incorporated into currently available nomograms to further increase the accuracy of such predictions.

D. Follow-Up Therapies

The disclosed methods can further include selecting subjects for treatment for prostate cancer, for example if the sample is diagnosed as having an aggressive prostate cancer (EGR+/PTEN−). Alternatively, the disclosed methods can further include selecting subjects for no treatment, if the sample is diagnosed as a non-aggressive prostate cancer (e.g., EGR−/PTEN+).

In some embodiments, the disclosed methods include one or more of the following depending on the patient's diagnosis or prognosis: a) prescribing a treatment regimen for the subject if the subject's determined diagnosis/prognosis is having an aggressive prostate cancer (such as treatment with one or more radiotherapies and/or chemotherapeutic agents, additional surgery, or combinations thereof); b) not prescribing a treatment regimen for the subject if the subject's determined diagnosis/prognosis is a non-aggressive prostate cancer; c) administering a treatment (such as treatment with one or more radiotherapies and/or chemotherapeutic agents, additional surgery, or combinations thereof) to the subject if the subject's determined diagnosis/prognosis is having an aggressive prostate cancer; and d) not administering a treatment regimen to the subject if the subject's determined diagnosis/prognosis is a non-aggressive prostate cancer. In an alternative embodiment, the method can include recommending one or more of (a)-(d). Thus, the disclosed methods can further include treating a subject for prostate cancer.

D. Compositions

Disclosed herein are genes (ERG and PTEN) the expression of which characterizes prostate cancer that has penetrated the capsule in subjects afflicted with the disease. Accordingly, compositions that facilitate the detection of such genes in biological samples are now enabled.

1. Kits

Kits useful for facilitating the practice of a disclosed method are also contemplated. In one embodiment, a kit is provided for detecting PTEN and ERG nucleic acid or protein molecules, for example in combination with one to ten (e.g., 1, 2, 3, 4, or 5) control genes or proteins (e.g., β-actin, GAPDH, SDHA, HPRT1, HBS1L, AHSP or combinations thereof). In yet other specific examples, kits are provided for detecting only PTEN and ERG nucleic acid or protein molecules. The detection means can include means for detecting a genomic alteration involving the gene and/or a gene expression product, such as an mRNA or protein. In particular examples, means for detecting a least ERG and PTEN are packaged in separate containers or vials. In some examples, means for detecting one or more ERG and PTEN genes or proteins are present on an array (discussed below).

Exemplary kits can include at least one means for detection of ERG and PTEN genes or gene products (for example in combination with other prostate cancer related genes/proteins or control genes/proteins) such as, at least two, at least three, at least four, or at least five detection means), such as means that permit detection of at least ERG and PTEN. In some examples, such kits can further include at least one means for detection of one or more (e.g., one to three) control genes or proteins. Detection means can include, without limitation, a nucleic acid probe specific for a genomic sequence including a disclosed gene, a nucleic acid probe specific for a transcript (e.g., mRNA) encoded by a disclosed gene, a pair of primers for specific amplification of a disclose gene (e.g., genomic sequence or cDNA sequence of such gene), an antibody or antibody fragment specific for a protein encoded by a disclosed gene.

In one example a kit can include means for detecting in a biological sample an ERG genomic sequence, ERG transcript or ERG protein, and means for detecting in a biological sample a PTEN genomic sequence, PTEN transcript or PTEN protein, or any combination thereof. For example, the kit can include a means for detecting in a biological sample an ERG transcript or protein and a means for detecting in a biological sample a PTEN transcript or protein, such as a nucleic acid probe specific for an ERG transcript and a nucleic acid probe specific for a PTEN transcript, such as a pair of primers for specific amplification of an ERG transcript and a pair of primers for specific amplification of a PTEN transcript, or such as an antibody specific for ERG protein and an antibody specific for a PTEN protein.

Particular kit embodiments can include, for instance, one or more (such as two, three, or four) detection means selected from a nucleic acid probe specific for an ERG transcript, a nucleic acid probe specific for a PTEN transcript, a pair of primers for specific amplification of an ERG transcript, a pair of primers for specific amplification of a PTEN transcript, an antibody specific for an ERG protein, and an antibody specific for a PTEN protein. Particular kit embodiments can further include, for instance, one or more (such as two or three) detection means selected from a nucleic acid probe specific for a control transcript, a pair of primers for specific amplification of control transcript, and an antibody specific for control protein. Exemplary control genes/proteins include GAPDH, SDHA, HPRT1, HBS1L, β-actin, and AHSP. In some examples, kits can further include, for instance, one or more (such as two or three) detection means selected from a nucleic acid probe specific for a prostate cancer related transcript, a pair of primers for specific amplification of prostate cancer related transcript, and an antibody specific for prostate cancer related protein. Exemplary prostate cancer related genes/proteins include GAS1; WNT5A; TK1; BRAF; ETV4; tumor protein p63; BCL-2; Ki67; ERK5; and PSA.

In some kit embodiments, the primary detection means (e.g., nucleic acid probe, nucleic acid primer, or antibody) can be directly labeled, e.g., with a fluorophore, chromophore, or enzyme capable of producing a detectable product (such as alkaline phosphates, horseradish peroxidase and others commonly know in the art).

Other kit embodiments will include secondary detection means; such as secondary antibodies (e.g., goat anti-rabbit antibodies, rabbit anti-mouse antibodies, anti-hapten antibodies) or non-antibody hapten-binding molecules (e.g., avidin or streptavidin). In some such instances, the secondary detection means will be directly labeled with a detectable moiety. In other instances, the secondary (or higher order) antibody will be conjugated to a hapten (such as biotin, DNP, and/or FITC), which is detectable by a detectably labeled cognate hapten binding molecule (e.g., streptavidin (SA) horseradish peroxidase, SA alkaline phosphatase, and/or SA QDot® Nanocrystals™). Some kit embodiments may include colorimetric reagents (e.g., DAB, and/or AEC) in suitable containers to be used in concert with primary or secondary (or higher order) detection means (e.g., antibodies) that are labeled with enzymes for the development of such colorimetric reagents.

In some embodiments, a kit includes positive or negative control samples, such as a cell line or tissue known to express or not express PTEN or ERG. In particular examples, control samples are FFPE. Exemplary samples include but are not limited to normal (e.g., non cancerous) cells or tissues, breast cancer cell lines or tissues, prostate cancer samples from subject known not to have capsular penetration, and prostate cancer samples from subject known to have capsular penetration.

In some embodiments, a kit includes instructional materials disclosing, for example, means of use of a nucleic acid probe or antibody that specifically binds a PTEN or ERG (e.g., mRNA or protein), or means of use for a particular primer or probe. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

Certain kit embodiments can include a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

2. Arrays

Microarrays for the detection of genes (e.g., genomic sequence and corresponding transcripts) and proteins are well known in the art. Microarrays include a solid surface (e.g., glass slide) upon which many (e.g., hundreds or even thousands) of specific binding agents (e.g., cDNA probes, mRNA probes, or antibodies) are immobilized. The specific binding agents are distinctly located in an addressable (e.g., grid) format on the array. The number of addressable locations on the array can vary, for example from at least two, to at least 10, at least 20, at least 30, at least 33, at least 40, at least 50, at least 75, at least 100, at least 150, at least 200, at least 300, at least 500, least 550, at least 600, at least 800, at least 1000, at least 10,000, or more. The array is contacted with a biological sample believed to contain targets (e.g., mRNA, cDNA, or protein, as applicable) for the arrayed specific binding agents. The specific binding agents interact with their cognate targets present in the sample. The pattern of binding of targets among all immobilized agents provides a profile of gene expression. In particular embodiments, various scanners and software programs can be used to profile the patterns of genes that are "turned on" (e.g., bound to an immobilized specific binding agent). Representative microarrays are described, e.g., in U.S. Pat. Nos. 5,412,087, 5,445,934, 5,744,305, 6,897,073, 7,247,469, 7,166,431, 7,060,431, 7,033,754, 6,998,274, 6,942,968, 6,890,764, 6,858,394, 6,770,441, 6,620,584, 6,544,732, 6,429,027, 6,396,995, and 6,355,431.

Disclosed herein are arrays, whether protein or nucleic acid arrays, for the detection at least ERG and PTEN. Particular array embodiments consist of nucleic probes or antibodies specific for ERG and PTEN expression products and one or more control products (e.g., mRNA, cDNA or protein). More particular array embodiments consist of nucleic probes or antibodies specific for ERG and PTEN expression products (e.g., mRNA, cDNA or protein) and one or more prostate cancer related products (e.g., mRNA, cDNA or protein). More particular array embodiments consist of nucleic probes or antibodies specific for ERG and PTEN expression products, one or more control products, and one or more prostate cancer related products (e.g., mRNA, cDNA or protein). More particular array embodiments consist of nucleic probes or antibodies specific for ERG and PTEN expression products (e.g., mRNA, cDNA or protein).

a. Nucleic Acid Arrays

In one example, the array includes nucleic acid probes that can hybridize to at least ERG and PTEN nucleic acids (such as genes). In particular examples, an array further includes probes that can specifically hybridize to other prostate marker nucleic acids, such as one or more of GAS1; WNT5A; TK1; BRAF; ETV4; tumor protein p63; BCL-2; Ki67; ERK5; and PSA. Certain of such arrays (as well as the methods described herein) can further include oligonucleotides specific for control genes (e.g., one or more of GAPDH, SDHA, HPRT1, HBS1L, β-actin, and AHSP).

In one example, a set of oligonucleotide probes is attached to the surface of a solid support for use in detection of ERG and PTEN, such as detection of nucleic acid sequences (such as genomic DNA, cDNA or mRNA) obtained from the subject (e.g., from a prostate cancer sample). Additionally, if an internal control nucleic acid sequence is used (such as a nucleic acid sequence obtained from a subject who has not had prostate cancer or a control gene nucleic acid sequence) a nucleic acid probe can be included to detect the presence of this control nucleic acid molecule.

The oligonucleotide probes bound to the array can specifically bind sequences obtained from the subject (such as a sample containing nucleic acids or nucleic acids isolated from the sample), or amplified from the subject, such as under high stringency conditions. Agents of use with the method include oligonucleotide probes that recognize ERG (including fusions of ERG, such as TMPRSS/ERG rearrangements). Such sequences can be determined by examining the known gene sequences, and choosing probe sequences that specifically hybridize to ERG or TMPRSS/ERG rearrangements, but not other gene sequences.

The methods and apparatus in accordance with the present disclosure take advantage of the fact that under appropriate conditions oligonucleotide probes form base-paired duplexes with nucleic acid molecules that have a complementary base sequence. The stability of the duplex is dependent on a number of factors, including the length of the oligonucleotide probe, the base composition, and the composition of the solution in which hybridization is effected. The effects of base composition on duplex stability can be reduced by carrying out the hybridization in particular solutions, for example in the presence of high concentrations of tertiary or quaternary amines. The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mis-matched duplexes may be substantially reduced.

The length of each oligonucleotide probe employed in the array can be selected to optimize binding of target sequences. An optimum length for use with a particular gene sequence under specific screening conditions can be determined empirically. Thus, the length for each individual element of the set of oligonucleotide sequences included in the array can be optimized for screening. In one example, oligonucleotide probes are at least 12 nucleotides (nt) in length, for example at least 20 nt, at least 50 nt, at least 100 nt, at least 1000 nt, at least 10,000 nt, or at least 100,000 nt, such as from about 20 to about 35 nt in length, about 25 to about 40 nt in length, about 25 to about 100 nt in length, about 1000 to about 6000 nt in length, about 10,000 to about 50,000 nt in length, about 10,000 to about 100,000 in length, about 10,000 to about 500,000 in length, or about 10,000 to about 1,000,000 in length.

The oligonucleotide probe sequences forming the array can be directly linked to the support. Alternatively, the oligonucleotide probes can be attached to the support by oligonucleotides (that do not non-specifically hybridize to the target gene sequences) or other molecules that serve as spacers or linkers to the solid support.

b. Protein Arrays

In another example, an array includes protein sequences (or a fragment of such proteins, or antibodies specific to such proteins or protein fragments), which specifically bind to ERG and PTEN, for example protein binding agents that can specifically bind to ERG and PTEN. In particular examples, an array includes protein binding agents that can recognize additional prostate cancer biomarkers, such as one or more of GAS1; WNT5A; TK1; BRAF; ETV4; ETV1; tumor protein p63; BCL-2; Ki67; ERK5; and PSA. Certain of such arrays (as well as the methods described herein) can further include protein binding agents specific for control proteins (e.g., one or more of GAPDH, SDHA, HPRT1, HBS1L, β-actin, and AHSP).

The proteins or antibodies forming the array can be directly linked to the support. Alternatively, the proteins or antibodies can be attached to the support by spacers or linkers to the solid support. Changes in protein expression can be detected using, for instance, a protein-specific binding agent, which in some instances is labeled. In certain examples, detecting a change in protein expression includes contacting a protein sample obtained from a prostate cancer sample of a subject with a protein-specific binding agent (which can be for example present on an array); and detecting whether the binding agent is bound by the sample and thereby measuring the levels of the target protein present in the sample. A increase in the level of ERG and a decrease in the level of PTEN in the test sample, relative to the level of the same protein found an analogous control sample (e.g., from a subject who does not have prostate cancer, or a non-cancerous prostate sample from the same patient which is adjacent to the prostate cancer), in particular examples indicates that the subject has a poor prognosis.

c. Array Substrate

The array solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (e.g., U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide or antibody thereto; amenability to "in situ" synthesis of biomolecules; being chemically inert such that at the areas on the support not occupied by the oligonucleotides or antibodies are not amenable to non-specific binding, or when non-specific binding occurs, such materials can be readily removed from the surface without removing the oligonucleotides or antibodies.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleic acid molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

d. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (e.g., U.S. Pat. No. 5,981,185). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for preparation of arrays are biaxially oriented polypropylene (BOPP) films; in addition to their durability, BOPP films exhibit a low background fluorescence.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (e.g., see U.S. Pat. No. 6,013,789). In another example, sequences are synthesized directly onto the support to provide the desired array (e.g., see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (e.g., see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

Oligonucleotide probes can be bound to the support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support. In particular examples, the oligonucleotide probes on the array include one or more labels, that permit detection of oligonucleotide probe:target sequence hybridization complexes.

3. Protein Specific Binding Agents

In some examples, the means used to detect ERG or PTEN is a protein specific binding agent, such as an antibody or fragment thereof. For example, antibodies or aptamers specific for ERG or PTEN (e.g., SEQ ID NO: 2, or 4, respectively), can be obtained from a commercially available source or prepared using techniques common in the art. Such specific binding agents can also be used in the prognostic methods provided herein.

Specific binding reagents include, for example, antibodies or functional fragments or recombinant derivatives thereof, aptamers, mirror-image aptamers, or engineered nonimmunoglobulin binding proteins based on any one or more of the following scaffolds: fibronectin (e.g., ADNECTINS™ or monobodies), CTLA-4 (e.g., EVIBODIES™), tendamistat (e.g., McConnell and Hoess, *J. Mol. Biol.*, 250:460-470, 1995), neocarzinostatin (e.g., Heyd et al., *Biochem.*, 42:5674-83, 2003), CBM4-2 (e.g., Cicortas-Gunnarsson et al., *Protein Eng. Des. Sel.*, 17:213-21, 2004), lipocalins (e.g., ANTICALINS™; Schlehuber and Skerra, Drug Discov. Today, 10:23-33, 2005), T-cell receptors (e.g., Chlewicki et al., *J. Mol. Biol.*, 346:223-39, 2005), protein A domain (e.g., AFFIBODIES™; Engfeldt et al., *ChemBioChem*, 6:1043-1050, 2005), Im9 (e.g., Bernath et al., *J. Mol. Biol.*, 345:1015-26, 2005), ankyrin repeat proteins (e.g., DARPins; Amstutz et al., *J. Biol. Chem.*, 280:24715-22, 2005), tetratricopeptide repeat proteins (e.g., Cortajarena et al., *Protein Eng. Des. Sel.*, 17:399-409, 2004), zinc finger domains (e.g., Bianchi et al., *J. Mol. Biol.*, 247:154-60, 1995), pVIII (e.g., Petrenko et al., *Protein Eng.*, 15:943-50, 2002), GCN4 (Sia and Kim, *Proc. Natl Acad. Sci. USA*, 100:9756-61, 2003), avian pancreatic polypeptide (APP) (e.g., Chin et al., *Bioorg. Med. Chem. Lett.*, 11:1501-5, 2001), WW domains, (e.g., Dalby et al., *Protein Sci.*, 9:2366-76, 2000), SH3 domains (e.g., Hiipakka et al., *J. Mol. Biol.*, 293:1097-106, 1999), SH2 domains (Malabarba et al., *Oncogene*, 20:5186-5194, 2001), PDZ domains (e.g., TELOBODIES™; Schneider et al., *Nat. Biotechnol.*, 17:170-5, 1999), TEM-1 β-lactamase (e.g., Legendre et al., *Protein Sci.*, 11:1506-18, 2002), green fluorescent protein (GFP) (e.g., Zeytun et al., Nat. Biotechnol., 22:601, 2004), thioredoxin (e.g., peptide aptamers; Lu et al., Biotechnol., 13:366-372, 1995), Staphylococcal nuclease (e.g., Norman, et al., *Science*, 285:591-5, 1999), PHD fingers (e.g., Kwan et al., *Structure*, 11:803-13, 2003), chymotrypsin inhibitor 2 (CI2) (e.g., Karlsson et al., *Br. J. Cancer*, 91:1488-94, 2004), bovine pancreatic trypsin inhibitor (BPTI) (e.g., Roberts, *Proc. Natl. Acad. Sci. USA*, 89:2429-33, 1992) and many others (see review by Binz et al., *Nat. Biotechnol.*, 23(10): 1257-68, 2005 and supplemental materials).

Specific binding reagents also include antibodies. The term "antibody" refers to an immunoglobulin molecule (or combinations thereof) that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), single chain Fv antibodies (scFv), polypeptides that contain at least a portion of an immunoglobulin that is sufficient to confer specific antigen binding to the polypeptide, and antigen binding fragments of antibodies. Antibody fragments include proteolytic antibody fragments [such as F(ab')2 fragments, Fab' fragments, Fab'-SH fragments, Fab fragments, Fv, and rIgG], recombinant antibody fragments (such as sFv fragments, dsFv fragments, bispecific sFv fragments, bispecific dsFv fragments, diabodies, and triabodies), complementarity determining region (CDR) fragments, camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

A Fab fragment is a monovalent fragment consisting of the VL, VH, CL and CH1 domains; a F(ab')2 fragment is a bivalent fragment comprising two Fab fragments linked by a disulfide bridge at the hinge region; an Fd fragment consists of the VH and CHI domains; an Fv fragment consists of the VL and VH domains of a single arm of an antibody; and a dAb fragment consists of a VH domain (see, e.g., Ward et al., Nature 341:544-546, 1989). A single-chain antibody (scFv) is an antibody in which a VL and VH region are paired to form a monovalent molecule via a synthetic linker that enables them to be made as a single protein chain (see, e.g., Bird et al., *Science*, 242: 423-426, 1988; Huston et al., *Proc. Natl. Acad. Sci. USA*, 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA*, 90:6444-6448, 1993; Poljak et al., *Structure*, 2:1121-1123, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites.

In some examples, an antibody specifically binds to ERG or PTEN with a binding constant that is at least $10^3$ $M^{-1}$ greater, $10^4$ $M^{-1}$ greater or $10^5$ $M^{-1}$ greater than a binding constant for other molecules in a sample. In some examples, a specific binding reagent (such as an antibody (e.g., monoclonal antibody) or fragments thereof) has an equilibrium constant ($K_d$) of 1 nM or less. For example, a specific binding agent may bind to a target protein with a binding affinity of at least about $0.1 \times 10^{-8}$ M, at least about $0.3 \times 10^{-8}$M, at least about $0.5 \times 10^{-8}$M, at least about $0.75 \times 10^{-8}$ M, at least about $1.0 \times 10^{-8}$M, at least about $1.3 \times 10^{-8}$ M at least about $1.5 \times 10^{-8}$M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Methods of generating antibodies (such as monoclonal or polyclonal antibodies) are well established in the art (for example, see Harlow and Lane, *Antibodies: A Laboratory Manual*, Cold Spring Harbor Laboratory, New York, 1988). For example peptide fragments of ERG or PTEN (e.g., fragments of SEQ ID NO: 2 or 4, respectively) can be conjugated to carrier molecules (or nucleic acids encoding such epitopes or conjugated RDPs) can be injected into non-human mammals (such as mice or rabbits), followed by boost injections, to produce an antibody response. Serum isolated from immunized animals may be isolated for the polyclonal antibodies contained therein, or spleens from immunized animals may be used for the production of hybridomas and monoclonal antibodies. In some examples, antibodies are purified before use.

In one example, monoclonal antibody to ERG or PTEN (e.g., SEQ ID NO: 2 or 4, respectively), can be prepared from murine hybridomas according to the classical method of Kohler and Milstein (*Nature*, 256:495, 1975) or derivative methods thereof. Briefly, a mouse (such as Balb/c) is repetitively inoculated with a few micrograms of the selected peptide fragment (e.g., epitope of ERG or PTEN) or carrier conjugate thereof over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.*, 70:419, 1980), and derivative methods thereof. Selected positive clones can be expanded and their monoclonal antibody product harvested for use.

Commercial sources of antibodies include Ventana Medical Systems (AZ), Epitomics (CA), Biocare (CA), Santa Cruz Biotechnology, Inc. (Santa Cruz, Calif.), Cell Signaling Technology (Danvers, Mass.), and abcam (Cambridge, UK). Table 2 shows exemplary commercial sources of antibodies for ERG and PTEN. A specific ERG antibody is the Ventana/Epitomics Clone EPR 3864 and a specific PTEN antibody is the anti-PTEN rabbit monoclonal antibody (Cell Signaling Technology Clone 138G6; catalog #9559).

TABLE 2

Exemplary commercial sources of antibodies.

| Antibody type | | Source |
|---|---|---|
| ERG | Rabbit Monoclonal | Ventana (Epitomics EPR 3864). |
| | Mouse Monoclonal | Biocare (clone 9F4) |
| PTEN | Monoclonal | Santa Cruz Biotechnology, Inc. (sc-7974; sc-133197; sc-133242) |
| | Rabbit Monoclonal | Cell Signaling Technology (clone 138G6) |

Disclosed specific binding agents also include aptamers. In one example, an aptamer is a single-stranded nucleic acid molecule (such as, DNA or RNA) that assumes a specific, sequence-dependent shape and binds to a target protein (e.g., ERG or PTEN) with high affinity and specificity. Aptamers generally comprise fewer than 100 nucleotides, fewer than 75 nucleotides, or fewer than 50 nucleotides (such as 10 to 95 nucleotides, 25 to 80 nucleotides, 30 to 75 nucleotides, or 25 to 50 nucleotides). In a specific embodiment, disclosed specific binding reagents are mirror-image aptamers (also called a SPIEGELMER™). Mirror-image aptamers are high-affinity L-enantiomeric nucleic acids (for example, L-ribose or L-2'-deoxyribose units) that display high resistance to enzymatic degradation compared with D-oligonucleotides (such as, aptamers). The target binding properties of aptamers and mirror-image aptamers are designed by an in vitro-selection process starting from a random pool of oligonucleotides, as described for example, in Wlotzka et al., Proc. Natl. Acad. Sci. 99(13):8898-8902, 2002. Methods of generating aptamers are known in the art (see e.g., Fitzwater and Polisky (Methods Enzymol., 267:275-301, 1996; Murphy et al., Nucl. Acids Res. 31:e110, 2003).

In another example, an aptamer is a peptide aptamer that binds to a target protein (e.g., ERG or PTEN) with high affinity and specificity. Peptide aptamers include a peptide loop (e.g., which is specific for the target protein) attached at both ends to a protein scaffold. This double structural constraint greatly increases the binding affinity of the peptide aptamer to levels comparable to an antibody's (nanomolar range). The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

Specific binding agents optionally can be directly labeled with a detectable moiety. Useful detection agents include fluorescent compounds (including fluorescein, fluorescein isothiocyanate, rhodamine, 5-dimethylamine-1-napthalenesulfonyl chloride, phycoerythrin, lanthanide phosphors, or the cyanine family of dyes (such as Cy-3 or Cy-5) and the like); bioluminescent compounds (such as luciferase, green fluorescent protein (GFP), or yellow fluorescent protein); enzymes that can produce a detectable reaction product (such as horseradish peroxidase, β-galactosidase, luciferase, alkaline phosphatase, or glucose oxidase and the like), or radiolabels (such as $^3$H, $^{14}$C, $^{15}$N, $^{35}$S, $^{90}$Y, $^{99}$Tc, $^{111}$In, $^{125}$I, or $^{131}$I).

4. Nucleic Acid Probes and Primers

In some examples, the means used to detect PTEN and ERG is a nucleic acid probe or primer. For example, nucleic acid probes or primers specific for PTEN and ERG can be obtained from a commercially available source or prepared using techniques common in the art. Such agents can also be used in the methods provided herein.

Nucleic acid probes and primers are nucleic acid molecules capable of hybridizing with a target nucleic acid molecule (e.g., genomic target nucleic acid molecule). For example, probes specific for a PTEN or ERG gene, when hybridized to the target, are capable of being detected either directly or indirectly. Primers specific for PTEN or ERG, when hybridized to the target, are capable of amplifying the target gene, and the resulting amplicons capable of being detected either directly or indirectly. Thus probes and primers permit the detection, and in some examples quantification, of a target nucleic acid molecule, such as PTEN and ERG.

Probes and primers can "hybridize" to a target nucleic acid sequence by forming base pairs with complementary regions of the target nucleic acid molecule (e.g., DNA or RNA, such as genomic DNA, cDNA or mRNA), thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

Commercial sources of probes and primers include Ventana Medical Systems, AZ) and Vysis (IL). Table 3 shows exemplary PTEN and ERG primer pairs and Table 4 shows an exemplary CEN10 probe that can detect a PTEN deletion (if PTEN is intact 2 pairs of CEN10 and PTEN are expected on chromosome 10; if PTEN is heterozygous, 1 pair of PTEN/CEN10 and a single CEN10 on the other copy of chromosome 10 is expected; if PTEN is homozygous only 2 single CEN10 signals—one on each arm of chromosome 10).

TABLE 3

Exemplary primers for ERG and PTEN.

| Target gene | Forward Primer (SEQ ID NO:) | Reverse Primer) (SEQ ID NO: | Amplicon |
|---|---|---|---|
| ERG 5p | TCCTTCCCCATCGGTTT GTGGC (5) | ACGCAGAGATCAGTGA AGGGAT (6) | 525 bp |

TABLE 3-continued

Exemplary primers for ERG and PTEN.

| Target gene | Forward Primer (SEQ ID NO:) | Reverse Primer) (SEQ ID NO: | Amplicon |
|---|---|---|---|
| ERG 3p | GTTTCTACACACGTTG CCCACT (7) | TCAAAAGGAATCACAT TTACCACGGA (8) | 107 bp |
| PTEN | TGACACCATGCAATCT TAAAAGCTGA (9) | TGGGAAAGGATTGACA ACTAAGAGGA (10) | 310 bp |

TABLE 4

Exemplary probe for CEN10.

| CEN10 (pA10RP8 plasmid pool) | GAATTCTTCTGTCTAGCAGTAAATGAGAAATCCCGCTTCCAA CGAAGGCCTCAAACGGGTCTAACTAATCACTTGCAGACTTTA CAGACAGAGTCTTTCCAAACTGCTCTATGAAGAGAAAGGTGA AACTCTGTGAACTGAACGCACAGATGACAAAGCAGTTTCTGA GAATGCTTCTGTGTAGTTTTTACACGAAGATATTTCCATTTC AAAGATTAGCCTCAAATCGCTTGAAATCTCCACTTGCAAACT CCACAGAAAGAATTTTTCAAAACTGCTCTGTCTAAAGGAAGG TTCAACTCTGTGACTTGAATACACACAACACAAAGAAGTGAC TGA |
|---|---|

Methods of generating a probe or primer specific for a target nucleic acid (e.g., PTEN and ERG) are routine in the art (see e.g., Sambrook et al., (1989) Molecular Cloning, second edition, Cold Spring Harbor Laboratory, Plainview, N.Y.). For example, probes and primers can be generated that are specific for any of SEQ ID NOS: 1 or 3, such as a probe or primer specific for at least 12, at least 50, at least 100, or at least 1000 contiguous nucleotides of such sequence (or its complementary strand). Probes and primers are generally at least 12 nucleotides in length, such as at least 15, at least 18, at least 20, at least 25, at least 30, at least 100, at least 1000, at least 5000, or at least 6000 nucleotides, such as 12 to 100, 12 to 50, 12 to 30, 15 to 25, 100 to 10,000, 1000 to 10,000 or 1000 to 6000 nucleotides. In one example, a primer for detecting ERG or PTEN is about 25 to 27 bp. In one example the probe is a FISH probe of at least 1000 bp, such as at least 2000, at least 3000, at least 4000, at least 5000, or at least 6000, such as 1000 to 6000 bp, that covers from about 150 kb to 170 kb. Generally, probes include a detectable moiety or "label". For example, a probe can be coupled directly or indirectly to a "label," which renders the probe detectable. In some examples, primers include a label that becomes incorporated into the resulting amplicon, thereby permitting detection of the amplicon.

The following examples are provided to illustrate certain particular features and/or embodiments. These examples should not be construed to limit a disclosed invention to the particular features or embodiments described.

Example 1

Increased ERG and Decreased PTEN Protein Expression Associated with Prostate Cancer Capsular Penetration This example describes methods used to show that ERG over-expression and loss of PTEN expression is associated with capsular penetration in prostate cancer.

Prostate tissue samples from men were analyzed using IHC and antibodies specific for ERG and PTEN. Samples from 426 men who underwent open radical prostatectomy between 1997 and 2008 were obtained. The prostates were totally embedded in paraffin. Only samples in which data for capsular (CP) as well as non-capsular penetration (NCP) was available, were used for this analysis (see FIG. 1). Sections with no tumor tissue were excluded from this analysis. Of the 426 men, 90 had capsular penetration (CP) and 90 had pT3 lesions with an additional separate contralateral lesion (non-capsular penetration, NCP, see FIG. 1). 18 men have thus far shown biochemical recurrence. Capsular penetrating lesions and the corresponding contralateral lesions were evaluated for ERG rearrangement and PTEN status by IHC. Normal PTEN expression (PTEN Pos) and absence of ERG (ERG Neg) were used as the reference group.

Figure 2:
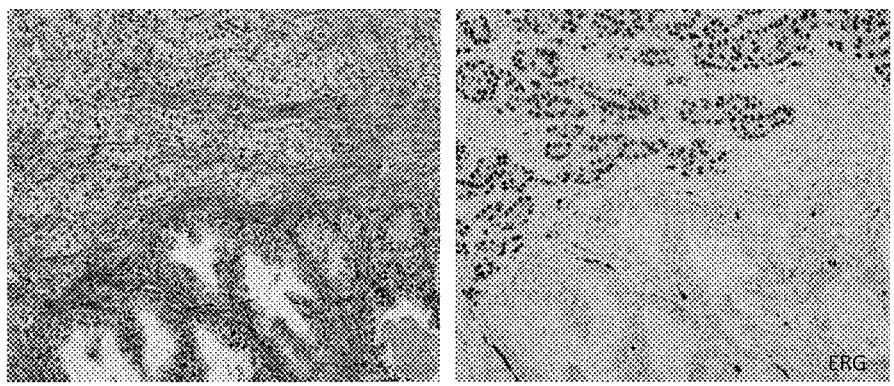
FIG. 2 is a digital image showing staining of prostate carcinoma with H&E (left) an ERG-specific antibody (right).

Formalin-fixed and paraffin-embedded (FFPE) samples analyzed using immunohistochemistry (IHC). ERG expression was analyzed using an anti-ERG rabbit monoclonal antibody (Ventana/Epitomics Clone EPR 3864) (FIG. 2). PTEN expression was analyzed using an anti-PTEN rabbit monoclonal antibody (Cell Signaling Technology Clone 138G6; catalog #9559) with a goat anti-rabbit secondary antibody conjugated to horseradish peroxidase (HRP, Ventana) and detected with the DAB chromogen. Specificity of signals was evaluated visually by a pathologist.

Figure 3:
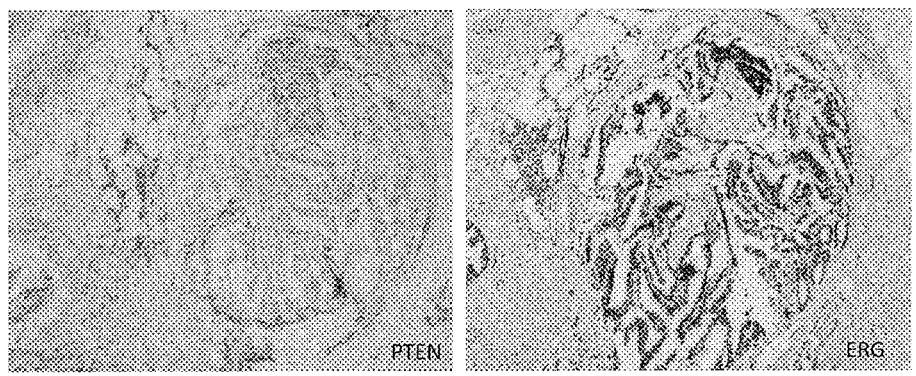
FIG. 3 is a digital image showing a prostate carcinoma from a case with capsule penetration and no detectable PTEN (left) and ERG-specific staining (right).
Figure 4:
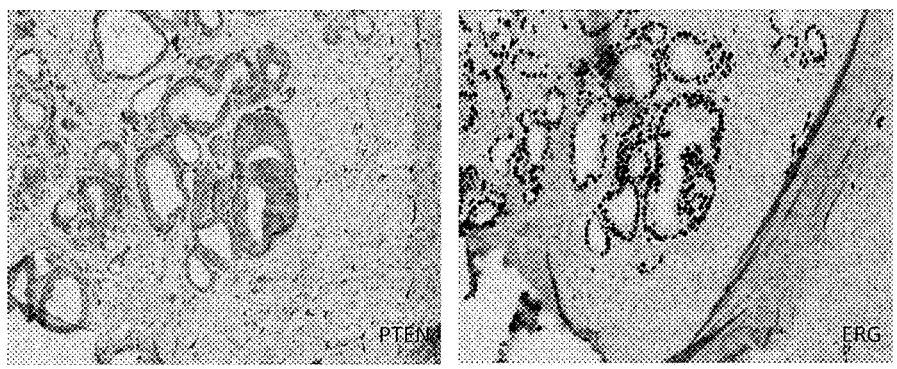
FIG. 4 is a digital image showing a prostate carcinoma with capsule penetration and detectable PTEN (left) and ERG-specific staining (right).
Figure 5:
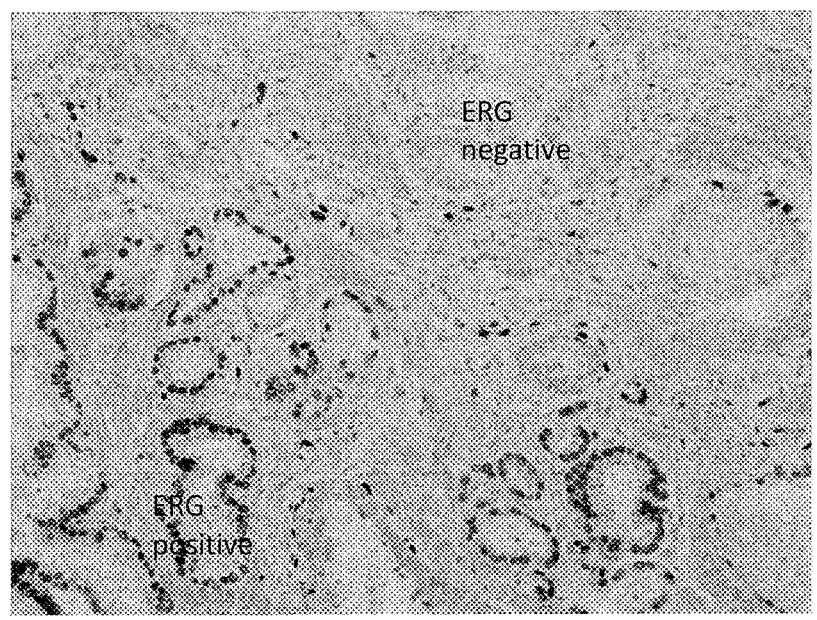
FIG. 5 is a digital image showing heterogeneous ERG expression in a prostate cancer that has not penetrated the capsule.
Figure 6:
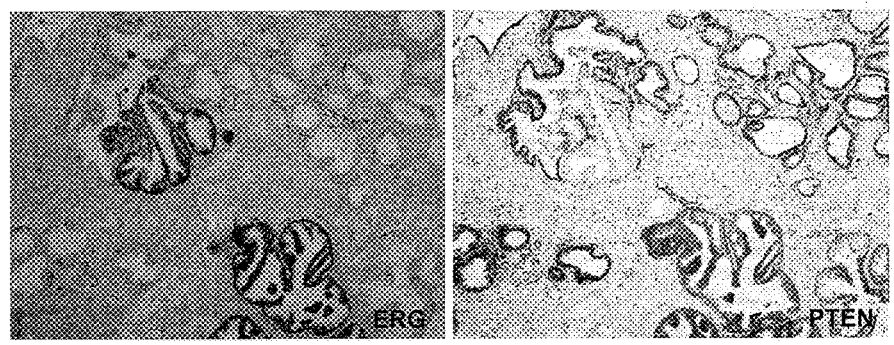
FIG. 6 is a digital image showing IHC results for ERG (left) and PTEN (right) expression in a prostate cancer sample.

As shown in FIG. 3, prostate capsule penetration samples are PTEN− and ERG+ in a representative sample. FIG. 4 shows a prostate capsule penetration sample that is PTEN+ and ERG+ in a representative sample. FIG. 5 shows heterogeneous ERG expression in a prostate capsule penetration sample. ERG expression was heterogeneous in 8/90 (9%) of CP and 7/90 (8%) of NCP lesions. FIG. 6 shows IHC results of ERG and PTEN staining. It was observed that invasive prostate cancers were associated with ERG positive high grade prostatic intraepithelial neoplasia (HGPIN) lesions in 21/90 (23.3%) of CP and 22/90 (24.4%) of NCP. This result indicates that ERG deletion and over-expression alone is unlikely to be prognostic of aggressive outcomes in the assessment of prostate cancer. All normal glands showed robust cytoplasmic staining for PTEN. Negative staining corresponding to lack of PTEN expression was observed in 31 of 90 (34%) of the capsular penetrating carcinoma lesions and 18 of 90 (20%) of the contralateral organ confined carcinoma lesions. The carcinoma lesions revealed heterogeneity of PTEN expression in 15 of 90 (16.6%) of the capsular penetrating carcinoma lesions and 11 of 90 (12.2%) of the contralateral organ confined carcinoma lesions.

Heterogeneity of the prostate cancer indicates that individual glands need to be assessed for the molecular rearrangements (example in ERG) and/or deletions (example in PTEN), including over-expression (example in ERG) and/or loss of expression (example in PTEN), or changes in morphology of the nuclei for the disease prognosis to be established.

If only ERG staining was analyzed in the absence of PTEN, there was no significant difference in the percentage of positive cases between the capsular penetration tumors and the non-capsular penetration tumors (p=0.54). There was no significant difference in the percentage of ERG positive tumors in the lesions with Gleason sum score ≥7 and <7.

As shown in Table 5, an odds ratio (OR) of 4.88 was observed for samples negative for PTEN protein expression and having increased ERG expression (indicating that capsular penetration is about 4.88-times more likely in lesions negative for PTEN expression and positive for ERG over-expression) than the normal reference (ERG−; PTEN+). This profile was generated after comparison with prostate cancer lesions demonstrating a normal expression profile for PTEN and ERG (Pos PTEN and Neg ERG). Based on these results, having an expression profile of PTEN loss and ERG over-expression is a risk factor for capsular penetration in prostate cancer.

TABLE 5

Association with Capsular Penetration

| Profile | Capsular Penetrated Lesion | Non-Capsular Penetrated Lesion | OR (95% CI) | p-value |
|---|---|---|---|---|
| ERG−/PTEN+ | 42 (47%) | 44 (49%) | | reference |
| ERG+/PTEN+ | 29 (32%) | 36 (40%) | 0.84 (0.42, 1.69) | 0.61 |
| ERG+/PTEN− | 14 (16%) | 3 (3%) | 4.88 (1.22, 28.0) | 0.01 |
| ERG−/PTEN− | 5 (6%) | 7 (8%) | 0.75 (0.17, 2.99) | 0.64 |
| Total | 90 (100%) | 90 (100%) | | |

Table 6 shows the association with Gleason sum score. Positive PTEN is associated with statistically significant lower Gleason sum score.

TABLE 6

Marker status by Gleason score.

| Marker | Status | Gleason sum scores, N (%) | | | | Total | p-value |
|---|---|---|---|---|---|---|---|
| | | 6 | 7 | 8 | 10 | | |
| ERG | Negative | 22 (46.1) | 13 (27.7) | 12 (25.5) | 0 | 47 (100) | 0.65 |
| | Positive | 22 (51.2) | 12 (27.9) | 8 (18.6) | 1 (2.3) | 43 (100) | |
| PTEN | Negative | 3 (15.8) | 7 (36.8) | 8 (42.1) | 1 (5.3) | 19 (100) | 0.003 |
| | Positive | 41 (57.8) | 18 (25.4) | 12 (16.9) | 0 | 71 (100) | |

Figure 7:
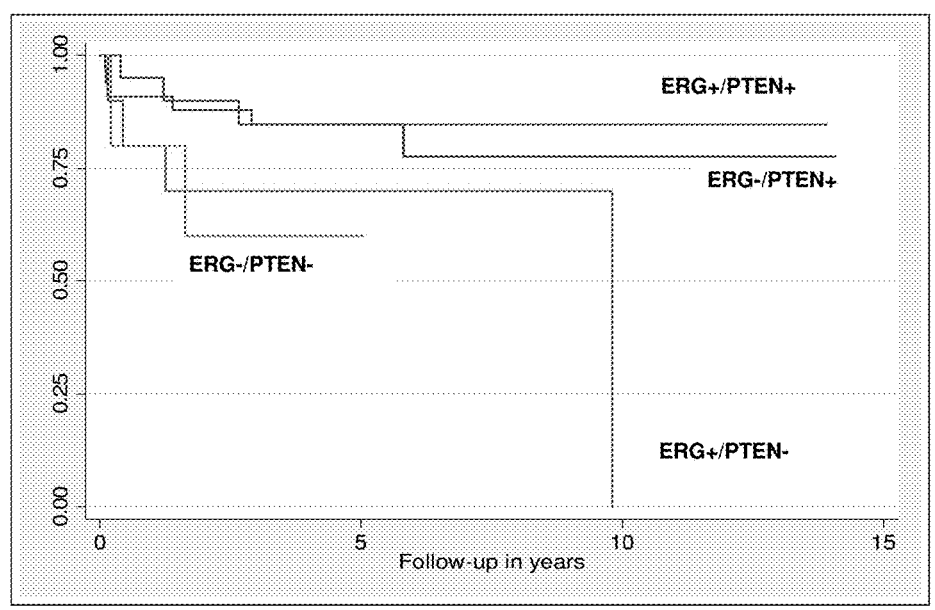
FIG. 7 is a graph showing that ERG+ and PTEN− prostate cancers are very highly aggressive, as indicated by early biochemical recurrence.

FIG. 7 shows Kaplan-Meier plots showing estimates for biochemical recurrence by ERG/PTEN profile of the capsular penetrated lesion. As shown in FIG. 7, PTEN-prostate cancers (such as those that are ERG+ or ERG−) are very highly aggressive, as indicated by increased incidences of biochemical recurrence (such as 1, 3 or 5 years post-prostatectomy). For example, at 5-years post-prostatectomy, patients with ERG+/PTEN+ or ERG−/PTEN+ tumors had a lower rate of biochemical recurrence than patients with ERG−/PTEN− or ERG+/PTEN− tumors (which have a higher rate of biochemical recurrence).

Example 2

Increased ERG and Decreased PTEN Genomic Expression Associated with Prostate Cancer Capsular Penetration A subset of recurrent cases was subjected to four color quantum dot FISH for evaluation of ERG gene rearrangement and PTEN gene deletions.

Figure 8:
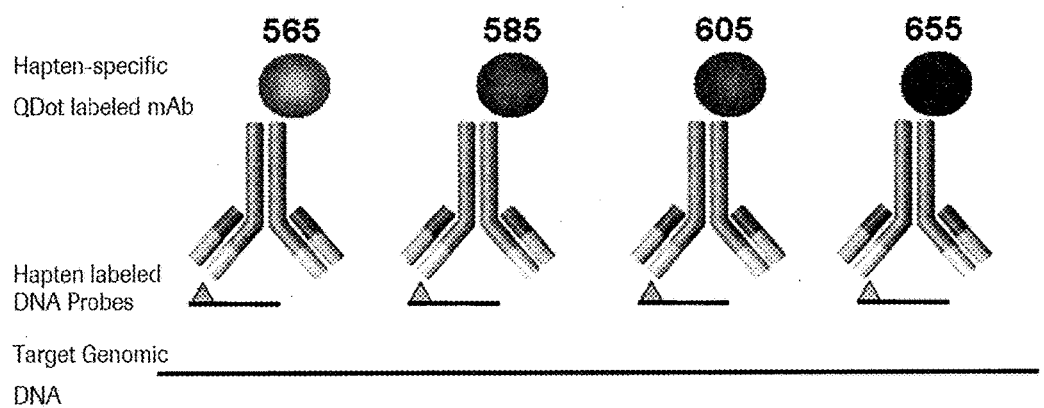
FIG. 8 is a schematic drawing showing the quantum dot FISH detection platform used to detect ERG and PTEN genomic DNA.

ERG gene rearrangements and PTEN deletions were detected in a simultaneous four probe/four Quantum Dot FISH assay (Benchmark®XT, Ventana) (FIGS. 8 and 9), essentially as described in Svensson et al. (*Lab. Invest.* 91:404-12, 2011, herein incorporated by reference) with the exception that FISH probes for 3p and 5'ERG were used together with those for PTEN and CEN10. ERG probe locations have been described (Tomlins et al. *Science* 310 (5748):644-8, 2005, herein incorporated by reference).

PTEN FISH probes are located on 10q23.31 and were derived from BAC clones RP11-659F22, RP11-210E13, CTD-2557P6, CTD-3243P1, and RP11-765C10 (LifeTechnologies, OR). The CEN10 (centromere 10) probe is inserted in a DNA plasmid pA10RP8 (ATCC, VA). All probes were purified and labeled using nick translation. Specifically, 5p ERG was labeled with dUTP DIG (digoxigenin, Roche), 3pERG with dCTP DNP (dinotrophenyl, Ventana), PTEN with dUTP TS (thiazole sulphonamide, Ventana), and CEN10 with dUTP NP (nitropyrazole, Ventana).

Detection was conducted online as a part of the automated protocol with monoclonals to DIG (mouse mAb, Roche), DNP (rat mAb LO-DNP, U Louvain, Brussels), TS (clone #13A06-01E11, Ventana) and NP (clone #806263, Ventana) conjugated to Quantum Dot 565, Quantum Dot 655, Quantum Dot 605, and Quantum Dot 585 respectively. All antibody conjugations are conducted using 30n PEGylated Quantum dots (Life Technologies, OR) and purified monoclonal antibodies. Quantum Dot-DAPI (Ventana) was applied online to counter-stain nuclei for evaluation and imaging. Regions of interest were selected in DAPI stained nuclei with 30 to 100 nuclei evaluated per case.

Concordance between FISH and IHC methods was observed. Of the 22 FISH samples there were 3 ERG and 6 PTEN tests which were non-informative. Of the 19 informative ERG FISH tests, 16 (84%) were concordant with the IHC result. Of the 6 ERG rearranged cases, 5 were deleted and 1 was break apart. Of the 16 informative PTEN FISH results 14 (88%) were concordant with the IHC result.

In summary, the lack of PTEN expression is associated with increased risk of capsular penetration, and men with an ERG+/PTEN− tumor have a higher risk of prostate cancer capsular penetration and earlier biochemical recurrence of prostate cancer.

Example 3

In Situ Hybridization to Detect Expression

This example provides exemplary methods that can be used to detect gene expression using in situ hybridization, such as FISH or CISH. Although particular materials and methods are provided, one skilled in the art will appreciate that variations can be made.

Prostate cancer tissue samples (e.g., samples that have penetrated the capsule), such as FFPE samples, are mounted onto a microscope slide, under conditions that permit detection of nucleic acid molecules present in the sample. For example, cDNA or mRNA in the sample can be detected. The slide is incubated with nucleic acid probes that are of sufficient complementarity to hybridize to cDNA or mRNA in the sample under very high or high stringency conditions.

Probes can be RNA or DNA. Separate probes that are specific for ERG and PTEN nucleic acid sequences (e.g., human sequences) are incubated with the sample simultaneously or sequentially, or incubated with serial sections of the sample. For example, each probe can include a different fluorophore or chromogen to permit differentiation between the three probes. After contacting the probe with the sample under conditions that permit hybridization of the probe to its gene target, unhybridized probe is removed (e.g., washed away), and the remaining signal detected, for example using microscopy. In some examples, the signal is quantified.

In some examples, additional probes are used, for example to detect expression of one or more other prostate cancer related genes or one or more control genes (e.g., β-actin). In some examples, expression of ERG and PTEN is also detected (using the same probes) in a control sample, such as a breast cancer cell, a prostate cancer cell from a subject who does not have an aggressive prostate cancer that has penetrated the prostatic capsule, a prostate cancer cell from a subject who has an aggressive prostate cancer that has penetrated the prostatic capsule, a non-cancer cell adjacent to the tumor, or a normal (non-cancer) cell.

The resulting hybridization signals for ERG and PTEN are compared to a control, such as a value representing ERG and PTEN expression in a normal (non-cancerous) prostate sample, such as a prostate sample that is ERG−/PTEN+. If increased expression of ERG, and decreased expression of PTEN, relative to a value representing ERG and PTEN expression in a normal prostate sample, this indicates that the subject has a poor prognosis (e.g., less than a 1 or 2 year survival) as the cancer is likely to recur. Similarly, if ERG and PTEN expression are similar relative to a value representing ERG and PTEN expression in a prostate cancer cell from a subject who has an aggressive prostate cancer that has penetrated the prostatic capsule (e.g., an ERG+/PTEN− prostate cancer sample), this indicates that the subject has a poor prognosis (e.g., the cancer is likely to recur, metastasize, and/or the patient has a shorter life expectancy). If ERG and PTEN expression are similar (e.g., no more than a 2-fold difference) relative to a value representing ERG and PTEN expression in a prostate cancer sample from a subject who does not have an aggressive prostate cancer that has penetrated the prostatic capsule, this indicates that the subject has a good prognosis (e.g., the cancer is not likely to recur, not metastasize, and/or the patient has a longer life expectancy).

Example 4

Nucleic Acid Amplification to Detect Expression

This example provides exemplary methods that can be used to detect gene expression using nucleic acid amplification methods, such as PCR. Amplification of target nucleic acid molecules in a sample can permit detection of the resulting amplicons, and thus detection of expression of the target nucleic acid molecules. Although particular materials and methods are provided, one skilled in the art will appreciate that variations can be made.

RNA is extracted from a prostate cancer tissue sample (such as one that has penetrated the capsule), such as FFPE samples or fresh tissue samples (e.g., surgical specimens). Methods of extracting RNA are routine in the art, and exemplary methods are provided elsewhere in the disclosure. For example RNA can be extracted using a commercially available kit. The resulting RNA can be analyzed as described in Example 1 to determine if it is of an appropriate quality and quantity.

The resulting RNA can be used to generate DNA, for example using RT-PCR, such as qRT-PCR. Methods of performing PCT are routine in the art. For example, the RNA is incubated with a pair of oligonucleotide primers specific for the target gene (e.g., ERG and PTEN). Such primers are of sufficient complementarity to hybridize to the RNA under very high or high stringency conditions. Primer pairs specific for ERG and PTEN nucleic acid sequences (e.g., human sequences) can be incubated with separate RNA samples (e.g., three separate PCR reactions are performed), or a plurality of primer pairs can be incubated with a single sample (for example if the primer pairs are differentially labeled to permit a discrimination between the amplicons generated from each primer pair). For example, each primer pair can include a different fluorophore to permit differentiation between the amplicons. Amplicons can be detected in real time, or can be detected following the amplification reaction. Amplicons are usually detected by detecting a label associated with the amplicon, for example using spectroscopy. In some examples, the amplicon signal is quantified.

In some examples, additional primer pairs are used, for example to detect expression of one or more other prostate cancer related genes, or one or more control genes (e.g., β-actin). In some examples, expression of ERG and PTEN is also detected (using the same probes) in a control sample, such as a breast cancer cell, a prostate cancer cell from a subject who does not have an aggressive prostate cancer that has penetrated the prostatic capsule, a prostate cancer cell from a subject who has an aggressive prostate cancer that has penetrated the prostatic capsule, a non-cancer cell adjacent to the tumor, or a normal (non-cancer) cell.

The resulting amplicon signals for ERG and PTEN are compared to a control, such as a value or range of values representing ERG and PTEN expression in a normal (non-cancerous) sample (e.g., a sample that is ERG−/PTEN+). If increased expression of ERG, and decreased expression of PTEN, relative to a value representing ERG and PTEN expression in a normal sample, this indicates that the subject has a poor prognosis (e.g., less than a 1 or 2 year survival) as the cancer is likely to recur. Similarly, if ERG and PTEN expression are similar relative to a value representing ERG and PTEN prostate cancer cell from a subject who has an aggressive prostate cancer that has penetrated the prostatic capsule, this indicates that the subject has a poor prognosis (e.g., the cancer is likely to recur, metastasize, and/or the patient has a shorter life expectancy). If ERG and PTEN expression are similar (e.g., no more than a 2-fold difference) relative to a value representing ERG and PTEN expression in a prostate cancer sample from a subject who does not have an aggressive prostate cancer that has penetrated the prostatic capsule, this indicates that the subject has a good prognosis (e.g., the cancer is not likely to recur, not metastasize, and/or the patient has a longer life expectancy).

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A kit for predicting the likelihood of prostate cancer progression, comprising:
   means for detecting in a biological sample an Ets related gene (ERG) genomic sequence, ERG transcript or ERG protein;
   means for detecting in a biological sample a phosphatase and tensin homolog (PTEN) genomic sequence, PTEN transcript or PTEN protein; and
   at least one positive control sample, wherein the positive control sample comprises a prostate cancer sample from a subject known to have capsular penetration.

2. The kit of claim 1, further comprising a negative control sample.

3. The kit of claim 2, wherein the negative control sample comprises a prostate cancer sample from a subject known not to have capsular penetration.

4. The kit of claim 1, wherein the kit comprises:
   a means for detecting in a biological sample an ERG transcript or protein; and
   a means for detecting in a biological sample a PTEN transcript or protein.

5. The kit of claim 1, wherein the kit comprises:
   a nucleic acid probe specific for ERG transcript and a nucleic acid probe specific for PTEN transcript;
   a pair of primers for specific amplification of an ERG transcript and a pair of primers for specific amplification of a PTEN transcript; or
   an antibody specific for ERG protein and an antibody specific for a PTEN protein.

6. The kit of claim 5, wherein the antibody specific for ERG protein comprises a label and the antibody specific for PTEN protein comprises a label.

7. The kit of claim 6, wherein the label is a radioactive isotope, fluorophore, chromophore, ligand, chemiluminescent agent, enzyme, or combination thereof.

8. The kit of claim 5, wherein the nucleic acid probe specific for ERG transcript comprises a label and the nucleic acid probe specific for PTEN transcript comprises a label.

9. The kit of claim 8, wherein the label is a radioactive isotope, fluorophore, chromophore, ligand, chemiluminescent agent, enzyme, or combination thereof.

10. The kit of claim 5, wherein the pair of primers for specific amplification of ERG transcript comprise a label and the pair of primers for specific amplification of PTEN transcript comprise a label.

11. The kit of claim 10, wherein the label is a radioactive isotope, fluorophore, chromophore, ligand, chemiluminescent agent, enzyme, or combination thereof.

12. The kit of claim 1, wherein the kit comprises at least two detection means selected from the group consisting of:
a nucleic acid probe specific for ERG transcript, a nucleic acid probe specific for PTEN transcript, a pair of primers for specific amplification of ERG transcript, a pair of primers for specific amplification of PTEN transcript, an antibody specific for ERG protein, and an antibody specific for a PTEN protein.

13. The kit of claim 1, further comprising a detection means selected from the group consisting of:
a nucleic acid probe specific for a control transcript, a pair of primers for specific amplification of a control transcript, and an antibody specific for a control protein.

14. The kit of claim 13, wherein the control transcript or control protein is β-actin, glyceraldehyde 3-phosphate dehydrogenase (GAPDH), succinate dehydrogenase (SDHA), hypoxanthine phosphoribosyl transferase 1 (HPRT1), HBS1-like protein (HBS1L), alpha haemoglobin stabilizing protein (AHSP) or a combination thereof.

15. The kit of claim 1, further comprising a detection means selected from the group consisting of:
a nucleic acid probe specific for a prostate cancer-related gene transcript, a pair of primers for specific amplification of a prostate cancer-related gene transcript, and an antibody specific for a prostate cancer-related protein.

16. The kit of claim 15, wherein the prostate cancer-related gene transcript or the prostate cancer-related protein is growth arrest specific 1 (GAS1); wingless-type MMTV integration site family member 5 (WNT5A); thymidine kinase 1 (TK1); V-raf murine sarcoma viral oncogene homolog B1 (BRAF); ETS translocation variant 4 (ETV4); tumor protein p63; B-cell lymphoma 2 (BCL-2); Ki67; extracellular signal-regulated kinase 5 (ERK6); or prostate specific antigen (PSA).

17. The kit of claim 1, wherein the means for detecting in a biological sample an ERG genomic sequence, ERG transcript or ERG protein and the means for detecting in a biological sample a PTEN genomic sequence, PTEN transcript or PTEN protein are covalently attached to a solid support.

18. A kit for predicting the likelihood of prostate cancer progression, comprising:
(a) means for detecting in a biological sample an ERG genomic sequence, ERG transcript or ERG protein;
(b) means for detecting in a biological sample a PTEN genomic sequence, PTEN transcript or PTEN protein; and
(c) a positive control sample and a negative control sample, wherein:
(i) the positive control sample comprises a prostate cancer sample from a subject known to have capsular penetration, and
(ii) the negative control sample comprises a prostate cancer sample from a subject known not to have capsular penetration.

* * * * *